(12) United States Patent
Hata et al.

(10) Patent No.: US 7,465,576 B2
(45) Date of Patent: Dec. 16, 2008

(54) METHOD FOR TREATING PERIODONTAL DISEASE WITH A BACTERIOCIDAL DISINFECTANT

(75) Inventors: Tadayo Hata, Tondabayashi (JP); Hitoshi Toshimori, Osaka (JP); Toshiyuki Maruoka, Toyonaka (JP)

(73) Assignee: BHPH Company Limited, Nassau (BS)

( * ) Notice: Subject to any disclaimer, the term of this patent is extended or adjusted under 35 U.S.C. 154(b) by 312 days.

(21) Appl. No.: 10/916,630

(22) Filed: Aug. 12, 2004

(65) Prior Publication Data

US 2006/0034783 A1 Feb. 16, 2006

(51) Int. Cl.
*C12N 1/20* (2006.01)
(52) U.S. Cl. .................... 435/252.9; 424/50; 424/93.45
(58) Field of Classification Search ........................ None
See application file for complete search history.

(56) References Cited

U.S. PATENT DOCUMENTS 6,296,881 B1 * 10/2001 Hata et al. .................. 424/647
6,333,188 B1 12/2001 Hata et al. .................. 435/252
2003/0203802 A1 * 10/2003 Westberg et al. .............. 494/43

FOREIGN PATENT DOCUMENTS

JP 2003-171292 6/2003

* cited by examiner

*Primary Examiner*—Ralph Gitomer
(74) *Attorney, Agent, or Firm*—Kratz, Quintos & Hanson, LLP

(57) ABSTRACT

A method for treating periodontal disease by first disinfecting the affected part with a bactericidal disinfectant containing ferric ions ($Fe^{+3}$) and L-ascorbic acid as the principal components and one or more of sorbic acid, benzoic acid and para-hydroxybenzoic acid esters, and then injecting a preparation containing a *Lactobacillus casei* into the affected part. Antibiotics are contained in the preparation, for enhancing the therapeutic effects.

4 Claims, 6 Drawing Sheets

METHOD FOR TREATING PERIODONTAL DISEASE WITH A BACTERIOCIDAL DISINFECTANT

BACKGROUND OF THE INVENTION

1. Field of the Invention

The present invention relates to a method for treating periodontal disease by first disinfecting the affected part with a bactericidal disinfectant having food additives as components, and then applying a novel *Lactobacillus* preparation to the treatment process.

2. Description of the Related Art

Periodontal disease, which is currently said to afflict 80% of adults, is a disease in which the surrounding tissues which support the teeth, namely the gums, cementum, periodontal membrane, alveolar bone and the like, become inflamed and gradually decay, and is caused by bacteria which colonize the periodontium and particular the grooves of the cervical part at the boundary of the teeth and gums by preference to form plaque. These bacteria produce toxins and enzymes which first cause localized inflammation of the gums or in other words gingivitis, and as this progresses gum pockets form in which the plaque grows, leading to onset of periodontal disease. As the symptoms progress, the pockets spread deeper, and inflammation spreads to the roots of the teeth and gradually destroys them so that sooner or later the teeth are lost. More specifically, in the early stages of periodontal disease, the gums of the cervical part to which plaque has adhered become red and swollen, losing their elasticity, and bleeding occurs during brushing. If nothing is done the plaque gradually grows to produce dental calculus which pushes open the cervical part, forming a periodontal pocket. The dental calculus forms a barrier which prevents brushing of the plaque underneath, and as the bacteria become more and more vigorous their toxins enlarge the pocket, inflammation spreads from the gums to the roots and the alveolar bone, where bleeding occurs along with pus leading to a perception of bad breath, and the surrounding teeth gradually become infected. If inflammation of the pocket becomes chronic, the alveolar bone which supports the roots begins to dissolve from the surface, while at the same time the gums become swollen and cannot fully support the teeth, which wobble and feel loose, and along with strong halitosis there is a sensation of pain when biting down hard. If this progresses, most of the alveolar bone dissolves, the roots are exposed, the teeth become more and more shaky so that hard foods cannot be eaten, and finally the teeth fall out one by one. Consequently, even today periodontal disease is recognized by experts as a typical model of a chronic infection which is difficult to cure completely.

The root cause of periodontitis is plaque, which is said to be an aggregation of about 400 different types of bacteria of which *Poryphyromonas gingivalis, Prevotella intermedia* and *Actinobacillus actinomycetemcomitans* are the most pathogenic for periodontitis, although it has been shown that the associated *Walinella recta, Bacteroides forsythus, Eikenella corrodens* and *Fusobacterium* and *Treponema* bacteria and the like are also involved. The primary difficulty in treating periodontal disease is its specificity. Because the teeth are directly connected to the inside of the body, when an inflammatory reaction is severe the body does not try to heal the periodontitis but instead forms a deep groove at the boundary between tooth and gum, breaks down the supporting tissues of the teeth, and in effect sacrifices the teeth to save the body just like a lizard breaking off its tail to survive. In other words, it is not an external enemy that destroys the tissues supporting the teeth, but an inflammation protecting the body from an external enemy. A mechanism operates in which a root which is contaminated by bacterial toxins and enzymes and becomes impregnated with them is not recognized as self by the body, but is removed together with the surrounding tissue as a causal factor. That is, a reaction aimed at healing actually aggravates the periodontal disease. Consequently, once the teeth affected by periodontal disease have all fallen out, the disease ceases and is completely cured.

Other factors include (1) the fact that the oral cavity is a favorable environment for bacterial growth and reproduction and is difficult to keep constantly clean, and bacteria with strong periodontal pathogenicity in particular adhere strongly to the teeth and gums by producing the sticky insoluble polysaccharide such as glucan, fructan etc., which also serves as a barrier to protect the pathogenic bacteria, (2) the fact that the toxins and enzymes produced thereby attack the periodontal tissue surreptitiously, so that the disease progresses with few subjective symptoms, while the appearance of symptoms is not uniform but includes various factors including soiling around the teeth, inflammation reactions, regression and aging of the gums and the like, and gum pockets are unlikely to close once they have formed, leading to repeated reoccurrence when combined with fact (1), (3) the fact that few dentists use suitable drugs for treatment in consultation with a specialist in bacteriology, (4) the fact that both doctors and patients make the easy assumption that in the worst case the teeth can be pulled, and (5) the fact that periodontal disease is not a local condition but a systemic disease which often involves for example diabetes and other endocrine disorders, genetic disorders, stress, osteoporosis, circulatory disorders and the like, and may not be completely curable by symptomatic therapy alone. The reason why it is said that periodontal disease cannot be cured unless therapy is started at an early stage is that it involves so many detrimental factors.

At present the principal form of initial treatment is by scaling and root planing to remove the plaque and dental calculus which nurture periodontal disease. Removal may be relatively easy in the case of supragingival calculus, which adheres to teeth surfaces above the gums, but subgingival calculus which adheres to the surfaces of teeth inside the gums (roots) is dense and hard, blackish-green in color and extremely adhesive, so the bacteria and their toxins cannot be easily removed with simple brushing. Therefore, methods have recently been adopted of efficiently destroying with ultrasound or lasers or dissolving with specialized chemicals. Subsequently a disinfectant or antibiotic is injected and fixed in the periodontal pocket until the site of inflammation heals. However, in cases in which the inflammation site reaches deep and favorable results are not obtained with the aforementioned treatment methods, the inflammation site or site of decay is excised surgically. The gum is then sutured or shaped by the insertion of artificial material. Advanced techniques which have been adopted include surgical techniques in conjunction with GTR (guided tissue regeneration), and to reinforce the surgical site, application of a type of protein called Emdogain® to reproduce an environment similar to the process of tooth development, which is expected to stimulate regeneration of periodontal tissue, but these are not effective in all cases of advanced periodontal disease, limiting their applicability. In any case, the basis of current therapy for periodontal disease is to control inflammation of the gums, arrest the progress of periodontal disease, regenerate lost periodontal tissue, improve external appearance, and maintain the newly-regenerated therapeutic tissue, but as mentioned above there are many systemic risk factor contributing to periodontal disease, so at present unfortunately there are no therapies effective enough to hold great promise, and many dentists feel it is enough if the status quo can be maintained without further deterioration.

Advanced techniques which have been adopted for periodontal disease include surgical techniques in conjunction with GTR (guided tissue regeneration), and to reinforce the surgical site, application of a type of protein called Emdogain® to reproduce an environment similar to the process of tooth development, which is expected to stimulate regeneration of periodontal tissue, but these are not effective in all cases of advanced periodontal disease, limiting their applicability. Therefore, the challenge is to develop methods of completely curing periodontal disease without surgery using drug only therapies which do not place a burden on the patient.

SUMMARY OF THE INVENTION

As a result of various studies aimed at overcoming these barriers to the treatment of periodontal disease, the present inventors discovered that instead of the disinfectants and antibiotics widely used in conventional therapeutic processes, the combined use of a bactericidal disinfectant (U.S. Pat. No. 6,296,881B1) developed by the inventors, gentle to mucous membranes, having food additives as its principal components and boasting characteristics lacking in conventional general-use disinfectants such as a high bactericidal effect not only against general pathogens but also against acid-fast bacteria and spore-forming bacteria despite displaying an extremely low toxicity, containing 500 ppm to 1,500 ppm of trivalent ferric ions, 500 ppm to 1,500 ppm of L-ascorbic acid, 200 ppm to 2,000 ppm of one or more members of sorbic acids, benzoic acids and para-hydroxybenzoic acid esters, together with a *Lactobacillus* (Patent Application 2003-203802) developed by the inventors inspired by intravaginal cleaning systems for *Doderlein bacilli*, exhibiting unique capabilities including having a high mucous membrane affinity, having economical effects by dramatically activating the organisms of humans, animals and plants to improve their growth and quality, and boosting the immune strength, periodontal disease from the initial stage to the advanced stage can be almost completely cured regardless of the technical abilities of the dentist as long as there is alveolar bone remaining to support the teeth, and they succeeded in providing a novel therapeutic method wherein the affected site of periodontal disease is first disinfected with a bactericidal disinfectant having food additives as its principal components, after which a preparation containing a novel *Lactobacillus* is infused into the affected site.

That is, the present invention provides a novel method for treating periodontal disease, wherein the affected part is first disinfected with a bactericidal disinfectant containing 500 ppm to 1,500 ppm of trivalent ferric ions and 500 ppm to 2,000 ppm of L-ascorbic acid as the principal components together with 200 ppm to 2,000 ppm of one or more members of the group consisting of sorbic acid, benzoic acid and para-hydroxybenzoic acid esters, and then a preparation containing a novel *Lactobacillus* casein, wherein FERM P-19443 is particularly preferable, capable of proliferating in a combination of 4 or less amino acids as a nitrogen source, and exhibiting the properties of the following (1) to (5) when cultured anaerobically for 48 hours at 37° C. in a MRS culture medium having a pH of 7.2 to 7.4 and consisting essentially of 10 g of meat extract, 5 g of yeast extract, 10 g of peptone, 0.2 g of $MgSO_4$-$7H_2O$, 0.5 g of $MnSO_4$-$5H_2O$, 5 g of sodium acetate, 2 g of diammonium citrate, 2 g of $KH_2PO_4$ and 20 g of glucose per liter of medium culture, is then infused into the affected part:

(1) The final pH is 4.0 or less and the maximum acidity is 1.5% or more;
(2) The preparation produces antibiotics;
(3) The maximum bacterial count is 50% or more of *E. coli* when a medium is inoculated with the same bacterial count of *E. coli* (ATCC 11775);
(4) Proliferation is possible even adding 5 wt % of sodium deoxycholate that is a type of bile acid at the beginning of the incubation.
(5) The preparation has at least one of the following properties in addition to the properties listed under 1 to 4 above:
  (a) It has ability to hydrolyze starch and produce lactic acid;
  (b) It has the effect of promoting the development of *chlorella*;
  (c) It has resistance against at least amoxicillin (AMPC), erythromycin (EM), fradiomycin (FRM) and minocycline (MINO).

A preparation containing the novel *Lactobacillus casei* should preferably contain antibiotics, and more preferably the antibiotics should be amoxicillin (AMPC), erythromycin (EM), fradiomycin (FRM) and cefaclor (CCL). It is also effective as a novel treatment method for periodontal disease that 100 g of a preparation containing the novel *Lactobacillus casei* should contain 2,000 mg amoxicillin (AMPC), 500 mg erythromycin (EM), 500 mg fradiomycin (FRM) and 500 mg cefaclor (CCL).

Before the advent of antibiotics there were almost no serious efforts to treat periodontal disease anywhere in the world. The bacteria in the lesions of periodontal disease were thought to also cause fatal diseases such as heart disease, and because of the emphasis on this danger teeth with severe cavities or periodontal disease were extracted without hesitation. Because of this theory dentistry for a long time was inclined less toward treatment and more towards tooth extraction and dealing with the results or in other words with dentures. This situation began to improve as antibiotics came into use, and in the nineteen-eighties as research on periodontal pathogens advanced it became more possible to predict the progress of the disease. Treatment principles were adopted to preserve the teeth, wherein basic treatment by removal of plaque and calculus was implemented, and if the inflammation improved and the periodontal pocket shrank as a result, it was possible to shore up the loose teeth so that they did not wobble, while if there was no improvement surgery was performed on the gums. It was also found that bacteria hidden inside the gums form special group structures and barriers, lessening the effects of antibacterials, bactericides and the like, and that the occurrence and progress of the disease is affected by factors such as the lifestyle of the patient, systemic conditions and genetic factors, so that the difficulty of curing periodontal disease was again emphasized and, perhaps out of a sense of helplessness, basic research and therapies for periodontal disease have advanced very little in the past decade.

On the other hand, as life expectancy has increased experts have begun to show the deep connections between the teeth and physical health, and an awareness has begun to permeate society that the teeth do not simply serve a chewing function but are central to life, so that in order to prevent dementia, cancer, cerebral hemorrhage, heart disease and the like it is important for medicine to treat bad teeth in order to draw out the body's natural healing powers and improve systemic functions. That is, it was recognized that the teeth are irreplaceable organs, and that mental and physical functions can be improved, aging prevented and happiness enhanced in life by means of the teeth. Tooth loss and cavities and the effects of imperfect artificial means used to repair them can induce a continuing and cumulative stress reaction in the body. As attention focuses on side-effects and drug problems, the development of the safe treatment method of the present invention which prevents tooth loss and places little mental, physical or economic burden on doctors or patients holds great promise for reforming treatment for periodontal disease (which has been scorned in the past as "cleaning up" treatment), and is sure to be a boon for the human race as it aims at a society in which it is normal to keep one's teeth.

The method for treating periodontal disease of the present invention is a superior method for treating periodontal disease wherein periodontal disease from the initial stage to the advanced stage can be almost completely cured regardless of the technical abilities of the dentist as long as there is alveolar bone remaining to support the teeth through combined use of a bactericidal disinfectant (U.S. Pat. No. 6,296,881B1) developed by the inventors which is gentle to mucous membranes and highly effective against pathogenic bacteria and a *Lactobacillus* (Patent Application 2003-203802) which has high mucous membrane affinity and specific effectiveness in place of disinfectants and antibiotics widely used in conventional therapeutic processes. Moreover, the method for treating periodontal disease of the present invention can also be performed in addition to conventional methods for treating periodontal disease.

DESCRIPTION OF THE PREFERRED EMBODIMENTS

Figure 1:
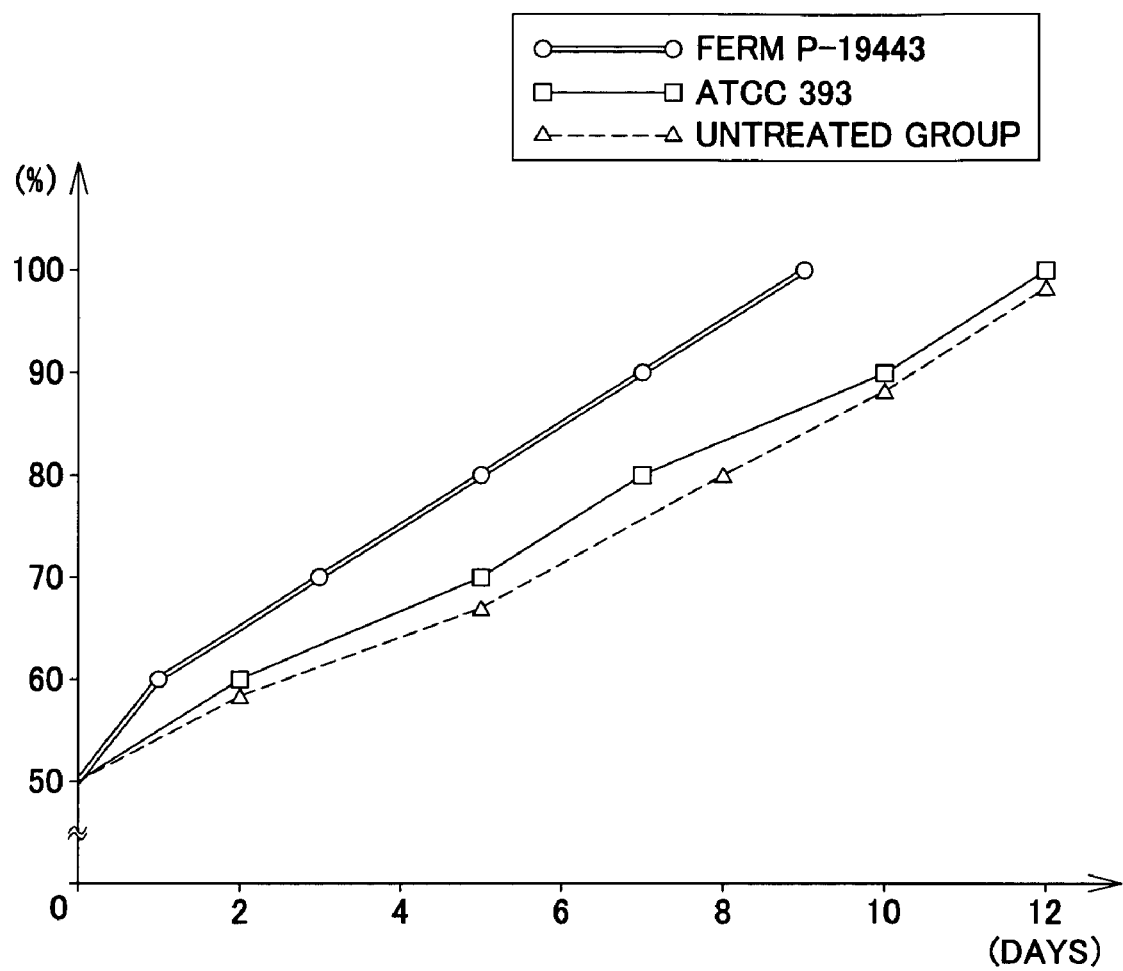
FIG. 1 shows regeneration of planaria.

The bactericidal disinfectant in the present invention (hereunder to be called "the present bactericidal disinfectant") is a bactericidal disinfectant containing 500 ppm to 1,500 ppm of ferric ions ($Fe^{3+}$) and 500 ppm to 2,000 ppm of L-ascorbic acid as the principal components along with 200 ppm to 2,000 ppm of one or more members of the group consisting of sorbic acid, benzoic acid and para-hydroxybenzoic acid esters. A U.S. patent has already been obtained therefor (U.S. Pat. No. 6,296,881B1), and its components are recognized as food additives in Japan. At present, disinfectants widely used in the medical field include alcohols, phenols, halogen compounds, quaternary ammonium salts, biguanide-based chemicals, aldehydes and the like, but none fulfill all the conditions of being excellent disinfectants, safe and of low toxicity, stable, cheap and the like. For example, the biguanide-based chemical sold under the trade name "Hibitane" is highly effective and of low toxicity and has been popular throughout the world for decades as an excellent disinfectant, but it has little effect against fungi and is ineffective against *Mycobacterium tuberculosis* and spores. Also, resistance has been noted in some ordinary bacteria, and has become a cause of hospital-acquired infection. The present bactericidal disinfectant, which was developed to compensate for conventional problems, kills most bacteria and fungi in a short period of time (only 10 seconds), and can eradicate spores in 1 to 120 minutes. Even though it exhibits such strong bactericidal ability, as shown below it is actually less toxic than all disinfectants currently in use.

(1) Effects on skin: No abnormalities were observed following application to the hind feet (foot pads) of mice twice a day for 6 months.

(2) Effects of oral administration: 1 ml/mouse was administered, but no toxicity was observed. This amount corresponds to 1.8 L for a human. The presumed $LD_{50}$ is 10 ml/mouse, corresponding to 18 L for a human.

(3) Effects or intraperitoneal administration: $LD_{50}$ was about 1 ml/mouse.

(4) Effects on cultured cells (animals): No impairment of cell proliferation was observed with a $10^3$ dilution of the concentration used. This is about 1/10 the toxicity of Hibitane.

(5) Effects on the human body:
  a) Disinfecting of hands and fingers: No abnormalities were observed even after continuous use every day for 7 years, apart from a slight irritation of the skin.
  b) Gargling: No abnormalities of the mucous membranes were observed after gargling morning and night for 7 years, and there were no side-effects or toxicity. No cavities occurred during this period and there was no need to go to the dentist.

Next, The results of various tests of the present bactericidal disinfectant performed with respect to periodontal disease are shown.

Test Example 1

A suspension ($1 \times 10^9$ cells/ml saline) of the test bacteria was prepared, and 2% by weight of the present bactericidal disinfectant was dripped into this bacterial liquid. Bacteria were removed over time with 1 platinum loop and seeded on various proliferating media, then cultured in an optimal environment, and bactericidal effect was observed according to the presence or absence of bacterial proliferation. The bactericidal disinfectant used in the experiments was set to the concentration for ordinary use. The results after 10 to 60 seconds of contact and the results after 1 to 120 minutes of contact are shown in Table 1. As shown in Table 1, the present bactericidal disinfectant kills most species of active bacteria within about 10 seconds, not excepting *P. gingivalis, P. intermedia* and *A. actimomycetemcomitans*, which are strong pathogens for periodontal disease. However, 1 to 120 minutes were required to kill the spores of sporulating bacteria, depending on the stage of sporulation. According to statistics, medical professionals and other humans take about 10 to 15 seconds for hand washing and gargling, and from this perspective the present bactericidal disinfectant would seem to be highly effective. When the same experiment was performed using the biguanide-based chemical Hibitane, 3% aqueous hydrogen peroxide and acrinol, which are disinfectants widely used in medical and dental clinics, 30 to 60 seconds was required for the bactericidal effects to appear, and as mentioned above Hibitane was ineffective against acid-fast bacteria and spores, while the 3% aqueous hydrogen peroxide was also ineffective against spores and required a minute or more to kill acid-fast bacteria. The results for acrinol were similar to those for 3% aqueous hydrogen peroxide.

TABLE 1

Bactericidal effects of bactericidal disinfectants

| | | | Bactericidal effects (presence or absence of bacteria growth) Contact time | | | | | | | |
|---|---|---|---|---|---|---|---|---|---|---|
| | | | Seconds | | | | Minutes | | | |
| | | | 10 | 20 | 30 | 60 | 1 | 30 | 60 | 120 |
| Gram-positive bacteria | S. aureus | | − | − | − | − | | | | |
| | S. aureus (MRSA) | | − | − | − | − | | | | |
| | S. pyogenes (group A beta-hemolytic streptococcus) | | − | − | − | − | | | | |
| | S. pneumoniae | | − | − | − | − | | | | |
| | E. faecalis | | + | + | − | − | | | | |
| | C. diphitheriae | | − | − | − | − | | | | |
| | L. monocytogenes | | − | − | − | − | | | | |
| Gram-negative bacteria | N. gonorrhoeae | | − | − | − | − | | | | |
| | E. coli O-157 | | − | − | − | − | | | | |
| | S. enteritidis | | − | − | − | − | | | | |
| | S. flexneri | | − | − | − | − | | | | |
| | V. parahaemoliticus | | − | − | − | − | | | | |
| | Ps. aeruginosa | | + | − | − | − | | | | |
| | S. marcescens | | − | − | − | − | | | | |
| | K. pneumoniae | | − | − | − | − | | | | |
| | L. pneumophila | | − | − | − | − | | | | |
| | P. gingivalis, A. actinomycetemcomitans (periodontal pathogens) | | − | − | − | − | | | | |
| | P. intermedia (periodontal pathogen) | | − | − | − | − | | | | |
| Acid-fast bacteria | M. tuberclosis | | + | + | − | − | | | | |
| | M. kansasii (atypical group I) | | + | + | − | − | | | | |
| | M. abium (atypical group III) | | + | + | − | − | | | | |
| Sporulating bacteria | B. subtilis | Germ cell | − | − | − | − | | | | |
| | | Spore | | | | | + | − | − | |
| | B. natto | Germ cell | + | + | + | − | | | | |
| | | Spore | | | | | + | − | − | |
| | C. perfrigens | Germ cell | + | + | + | − | | | | |
| | | Spore | | | | | + | − | − | |
| | C. tetani | Germ cell | + | + | + | − | | | | |
| | | Spore | | | | | + | − | − | |
| Fungi | C. albicans | | + | − | − | − | | | | |
| | T. interdigitale | | − | − | − | − | | | | |
| | A. fumigatus | | − | − | − | − | | | | |
| | C. neobormans[1] | | − | − | − | − | | | | |

Test Example 2

It is known that in general the effects of disinfectants are diminished by mixing with organic substance, particular proteins, so bactericidal effects were investigated in the presence of organic substance. First, skim milk and yeast extract were each added to the present bactericidal disinfectant in amounts of 1 ppm, 50 ppm and 100 ppm, while at the same time 2% by weight of $1 \times 10^9$ cells/ml saline of MRSA or E. coli O-157 as the test bacteria was dripped into these aqueous solutions. The contact time between the test bacteria and the present bactericidal disinfectant was 10 seconds to 5 minutes, and over time 10 μl of the test bacteria mixture was collected, seeded on respective suitable media and cultured at 37° C., and bactericidal effects were evaluated according to the presence or absence of bacterial growth. The results are as shown in Table 2: no effect was seen from the presence of organic substance when the concentration of organic substance was 1 ppm, while once the concentration of organic substance exceeded 50 ppm there was some effect but it was slight. The same experiment was performed with bacteria other than the two species mentioned above, with similar results. The same experiment was also performed using disinfectants widely used in dental clinics and the like, but using Hibitane the bacteria did not die after 1 minute of contact when the concentration exceeded 50 ppm, and depending on the type and amount of organic substance they even survived 5 minutes of contact. A similar tendency was seen with 3% aqueous hydrogen peroxide and acrinol as with Hibitane.

TABLE 2

Bactericidal effects in the presence of organic matter

| | Bactericidal effects (presence or absence of cell growth Contact time) | | | | | | |
|---|---|---|---|---|---|---|---|
| | Seconds | | | | Minutes | | |
| | 10 | 20 | 30 | 60 | 2 | 3 | 5 |
| S. aureus (MRSA) Skim milk | | | | | | | |
| 1 ppm | − | − | − | − | − | − | − |
| 50 ppm | + | + | − | − | − | − | − |
| 100 ppm | + | + | − | − | − | − | − |
| Yeast extract | | | | | | | |
| 1 ppm | − | − | − | − | − | − | − |
| 50 ppm | + | − | − | − | − | − | − |
| 100 ppm | + | + | − | − | − | − | − |
| E. coli O-157 Skim milk | | | | | | | |
| 1 ppm | − | − | − | − | − | − | − |
| 50 ppm | + | + | − | − | − | − | − |
| 100 ppm | + | + | − | − | − | − | − |
| Yeast extract | | | | | | | |
| 1 ppm | − | − | − | − | − | − | − |
| 50 ppm | + | − | − | − | − | − | − |
| 100 ppm | + | + | + | − | − | − | − |

Test Example 3

With regards to the putrefaction process of prepared food, we investigated whether or not the present bactericidal disinfectant could stop the progress of putrefaction when sprayed of food, and the degree of that bactericidal effect. Normally disinfectants are not applied to prepared food, but very often scraps of food become lodged in a periodontal pocket, providing a nutritional source for bacteria, and since the present bactericidal disinfectant is composed of compounds which are recognized as food additives, it is important to assess these effects. Just-prepared cooked rice, tofu (soybean curd), spinach with sesame dressing, and fried meat and vegetables were each crushed, homogenized, and left at 28° C. for use as the samples. After samples had been left for 5 hours, part of each was taken and used to measure bacterial viable cell number, while the respective disinfectants were sprayed uniformly on the remaining samples. Viable cell numbers were measured 1, 2 and 24 hours after spraying. Water alone was sprayed as a control. After samples had been left for 24 hours part of each was taken for measuring viable cell number, and the respective disinfectants were sprayed uniformly on the remaining samples. As when the samples were left for 5 hours, viable cell numbers were measured 1 hour, 2 hours and 24 hours after spraying. Water alone was sprayed as a control. Viable cell numbers were measured by the poured plate method using 5 g of each sample diluted by ordinary methods.

The degree of putrefaction of course differs depending on the preparation method, ingredients and environment, but in the case of the cooked rice in this experiment, the viable cell number immediately after preparation was $2 \times 10$ cells/g of sample, rising to $1 \times 10^3$ cells/g of sample after 5 hours, $5 \times 10^5$ cells/g of sample after 24 hours and $7 \times 10^6$ cells/g of sample after 48 hours. In the case of the tofu (soybean curd), the initial viable cell number was $2 \times 10^4$ cells/g of sample, rising to $8 \times 10^5$ cells/g of sample after 5 hours, $9 \times 10^7$ cells/g of sample after 24 hours, and $1 \times 10^9$ cells/g of sample after 48 hours, with considerable putrefaction. In the case of the spinach with sesame dressing, the viable cell number was $2 \times 10^3$ cells/g of sample immediately after preparation, rising to $5 \times 10^4$ cells/g of sample after 5 hours, $3 \times 10^7$ cells/g of sample after 24 hours and $2 \times 10^8$ cells/g of sample after 48 hours. In the case of the fried meat and vegetables, it was $5 \times 10$ cells/g of sample immediately after preparation, rising to $2 \times 10^3$ cells/g of sample after 5 hours and $2 \times 10^8$ cells/g of sample after 24 hours, at which point there was a slight smell of putrefaction, while after 48 hours putrefaction has progressed still further and the viable cell number had risen to $3 \times 10^9$ cells/g of sample.

The test results are shown in Table 3. When the disinfectant was sprayed at a point 5 hours after preparation when the bacteria had not proliferated greatly, the viable cell numbers immediately decreased to between 1/100 and 1/200 with some variation depending on the type of prepared food. After 1 hour they had decreased to between 1/1000 and 1/5000, and after 2 hours the cells had died off, dropping below 10 cells/g of sample. The surviving cells did not proliferate even after 24 hours. In the case of a food such as meat with a high protein content, a cell number of $7 \times 10^2$ cells/g sample (about 1%) survived even 2 hours after spraying of the disinfectant. 24 hours after preparation the viable cell numbers were on the order of $10^7$ to $10^8$, but were seen to decrease to 1/1000 to 1/10,000 immediately after spraying of the disinfectant, to 1/10,000 to 1/500,000 after 1 hour and to 1/300,000 to 1/2,000,000 after 2 hours. The viable cell numbers at this point were about $10^2$ cells/g of sample. After 24 hours the viable cell numbers were slightly higher than after 2 hours, but this is probably attributable not so much to proliferation of surviving cells as to dropping of cells from the air. Consequently, although complete eradication was not achieved, it can be said that bactericide was largely achieved. That is, there is the ability to halt development of putrefying bacteria in food and a bactericidal effect.

In addition to the present bactericidal disinfectant, the same experiment was performed using disinfectants widely used in dental clinics, with the results shown in Table 3. When Hibitane was sprayed, a similar tendency was observed although the rate of decrease in viable cell numbers was lower than with the present bactericidal disinfectant but the effect grew weaker over time and the bacteria began once more to proliferate. In other words, growth of putrefying bacteria in the food was suppressed to some extent, but there was no bactericidal effect in the real sense. With 3% aqueous hydrogen peroxide most of the bacteria survived immediately after spraying, and after 24 hours the food was almost at the point of putrefaction.

TABLE 3

Rise and fall of viable cell numbers in prepared food due to disinfectant

| Food | | | Water | The bactericidal disinfectant | Hibitane solution | 3% aqueous hydrogen peroxide |
|---|---|---|---|---|---|---|
| Cooked Rice | Just prepared: $2 \times 10$ | | | | | |
| | After 5 hours | $1 \times 10^3$ (spray) | | | | |
| | | Just after | $1 \times 10^3$ | $8 \times 10$ | $1 \times 10^2$ | $2 \times 10^2$ |
| | | 1 hr | $2.2 \times 10^3$ | $5 \times 10$ | $5 \times 10$ | $1 \times 10^2$ |
| | | 2 hrs | $7 \times 10^3$ | 0 | $2 \times 10$ | $1.8 \times 10^2$ |
| | | 24 hrs | $6 \times 10^6$ | 0 | $5 \times 10$ | $5 \times 10^4$ |
| | After 24 hours | $5 \times 10^5$ (spray) | | | | |
| | | Just after | $5.5 \times 10^5$ | $8 \times 10^3$ | $1 \times 10^4$ | $4 \times 10^4$ |
| | | 1 hr | $1.2 \times 10^6$ | $5 \times 10^2$ | $7 \times 10^2$ | $9 \times 10^3$ |
| | | 2 hrs | $2 \times 10^6$ | $1 \times 10^2$ | $5 \times 10^2$ | $2 \times 10^4$ |
| | | 24 hrs | $1 \times 10^8$ | $1 \times 10^2$ | $4 \times 10^3$ | $8 \times 10^5$ |
| | After 48 hours | $7 \times 10^6$ | | | | |
| TOFU(Soybean Curd) | Just prepared: $2 \times 10^4$ | | | | | |
| | After 5 hours | $8 \times 10^5$ (spray) | | | | |
| | | Just after | $1 \times 10^6$ | $3 \times 10^3$ | $8 \times 10^2$ | $5 \times 10^4$ |
| | | 1 hr | $3 \times 10^6$ | $1 \times 10^2$ | $5 \times 10$ | $2 \times 10^3$ |
| | | 2 hrs | $5 \times 10^6$ | 5 | $4 \times 10$ | $3 \times 10^4$ |
| | | 24 hrs | $1 \times 10^8$ | 8 | $2 \times 10^2$ | $6 \times 10^6$ |
| | After 24 hours | $9 \times 10^7$ (spray) | | | | |
| | | Just after | $9 \times 10^7$ | $6 \times 10^4$ | $5 \times 10^4$ | $7 \times 10^5$ |
| | | 1 hr | $1.2 \times 10^8$ | $4 \times 10^2$ | $5 \times 10^2$ | $3 \times 10^4$ |
| | | 2 hrs | $2 \times 10^8$ | $3 \times 10$ | $2 \times 10^2$ | $5 \times 10^4$ |
| | | 24 hrs | $2 \times 10^9$ | $1 \times 10^2$ | $3 \times 10^3$ | $1 \times 10^8$ |
| | After 48 hours | $1 \times 10^9$ | | | | |
| SPINACH WITH SESAME DRESSING | Just prepared: $2 \times 10^3$ | | | | | |
| | After 5 hours | $5 \times 10^4$ (spray) | | | | |
| | | Just after | $5 \times 10^4$ | $2 \times 10^2$ | $2 \times 10^2$ | $1 \times 10^3$ |
| | | 1 hr | $9 \times 10^4$ | $5 \times 10$ | $4 \times 10$ | $4 \times 10^2$ |
| | | 2 hrs | $1.5 \times 10^5$ | 0 | $3 \times 10$ | $5 \times 10^2$ |
| | | 24 hrs | $5 \times 10^7$ | $7 \times 10$ | $6 \times 10^2$ | $1 \times 10^5$ |
| | After 24 hours | $3 \times 10^7$ (spray) | | | | |
| | | Just after | $3 \times 10^7$ | $5 \times 10^3$ | $3 \times 10^4$ | $4 \times 10^4$ |
| | | 1 hr | $4 \times 10^7$ | $8 \times 10$ | $2 \times 10^2$ | $5 \times 10^3$ |
| | | 2 hrs | $6 \times 10^7$ | $2 \times 10$ | $1 \times 10^2$ | $5 \times 10^3$ |
| | | 24 hrs | $4 \times 10^8$ | $1 \times 10^2$ | $8 \times 10^3$ | $7 \times 10^6$ |
| | After 48 hours | $2 \times 10^8$ | | | | |
| FRIED MEAT AND VEGETABLES | Just prepared: $5 \times 10$ | | | | | |
| | After 5 hours | $2 \times 10^3$ (spray) | | | | |
| | | Just after | $2.5 \times 10^3$ | $1 \times 10^2$ | $2 \times 10^2$ | $5 \times 10^2$ |
| | | 1 hr | $6 \times 10^3$ | $5 \times 10$ | $5 \times 10$ | $2 \times 10^2$ |
| | | 2 hrs | $1 \times 10^4$ | $2 \times 10$ | $3 \times 10$ | $4 \times 10^2$ |
| | | 24 hrs | $3 \times 10^8$ | $7 \times 10^2$ | $5 \times 10^3$ | $5 \times 10^6$ |
| | After 24 hours | $2 \times 10^8$ (spray) | | | | |
| | | Just after | $2 \times 10^8$ | $1 \times 10^5$ | $7 \times 10^4$ | $6 \times 10^6$ |
| | | 1 hr | $4 \times 10^8$ | $4 \times 10^2$ | $5 \times 10^2$ | $5 \times 10^4$ |
| | | 2 hrs | $6 \times 10^8$ | $1 \times 10^2$ | $2 \times 10^2$ | $1 \times 10^5$ |
| | | 24 hrs | $4 \times 10^9$ | $2 \times 10^3$ | $5 \times 10^4$ | $4 \times 10^8$ |
| | After 48 hours | $4 \times 10^9$ | | | | |

The respective data for the present bactericidal disinfectant in Test examples 1 through 3 above promise a strong bactericidal effect with respect to periodontal pathogens hidden in the periodontal pocket. By contrast, disinfectants widely used in dentistry are somewhat effective when the periodontal pathogens lack a barrier, but when plaque or calculus has formed and when a nutrient source such as organic substance or food residue is present, this effect is dramatically less.

Based on the test results shown above, the efficacy of the respective bactericidal disinfectants was tested using as the test material plaque, which is considered the actual cause of periodontal disease.

Test Example 4

Plaque adhering to supragingival calculus was collected, sliced as is into 200 μm thick slices or ground to a fine powder with a grain size of 10 μm and soaked in 1 ml of the present bactericidal disinfectant, and the viable cell numbers contained therein were measured over time by ordinary methods. The results are as shown in Table 4: the viable cell number of $4 \times 10^9$ cells contained in 20 mg of sliced plaque was reduced by ¾ after 1 minute of immersion and to 1/5,000 after 5 minutes, and after 10 minutes all the cells were dead. The cells in the powdered plaque were all dead within 3 minutes. In other words, it was shown that the present bactericidal disinfectant penetrates the barrier and infiltrates the interior of the plaque to exercise a bactericidal effect on the bacteria within. In the case of Hibitane (Hibitane gel), 3% aqueous hydrogen peroxide and acrinol, which are widely used in dentistry, most of the bacteria on the surface of the plaque were eradicated within 3 minutes, but bacteria living inside resisted 60 minutes of immersion and half survived. In other words, they are not able to inflict critical damage on plaque, which is an aggregation of bacteria. When a similar test was performed on plaque adhering to subgingival calculus (which is dense and strong), all bacteria died within 15 minutes in the case of the sliced plaque and 3 minutes in the case of the powdered plaque. By contrast, with Hibitane solution and the like the bacteria endured 60 minutes of immersion as described above and continued to survive.

TABLE 4

Changes in viable cell numbers in plaque due to treatment with the bactericidal disinfectant

| | Viable cell numbers in 20 mg plaque | | | | | | |
|---|---|---|---|---|---|---|---|
| | Before treatment | After 1 min | After 3 min | After 5 min | After 10 min | After 15 min | After 30 min |
| Sliced plaque | $4 \times 10^9$ | $1 \times 10^9$ | $5 \times 10^7$ | $8 \times 10^5$ | 0 | 0 | 0 |
| Powdered plaque | $4 \times 10^9$ | $2 \times 10^8$ | 0 | 0 | 0 | 0 | 0 |

Next, 20 mg of plaque and 20 mg of yeast extract were mixed to simulate a case in which organic matter adheres to or is mixed with plaque adhering to calculus, and a test performed by the methods described above. The results were as shown in Table 5: there was almost no effect from the organic matter, with bacteria reduced to about $1/2,000$ after 5 minutes' immersion of the sliced plaque, and all bacteria eradicated after 10 minutes' immersion. In the case of the powdered plaque, all bacteria were eradicated after 3 minutes immersion. By contrast, with widely-used disinfectants 10 minutes were required to disinfect the surface of the plaque with organic matter present, and half of the interior bacteria survived. In other words, it was shown that as long as plaque is not completely eliminated by treatment, even if there appears to be a temporary improvement the condition will continue to occur

TABLE 5

Changes in viable cell numbers in plaque and organic matter due to treatment with the bactericidal disinfectant

| | Viable cell number in 20 mg plaque and 20 mg yeast extract | | | | | | |
|---|---|---|---|---|---|---|---|
| | Before treatment | After 1 min | After 3 min | After 5 min | After 10 min | After 15 min | After 30 min |
| Sliced plaque | $3.5 \times 10^9$ | $1.5 \times 10^9$ | $1 \times 10^8$ | $2 \times 10^6$ | 0 | 0 | 0 |
| Powdered plaque | $3.5 \times 10^9$ | $4 \times 10^8$ | 0 | 0 | 0 | 0 | 0 |

It is clear from the various tests performed in Test examples 1 through 4 above that the present bactericidal disinfectant inflicts critical damage on active-type bacteria existing in a variety of environments. Periodontal pathogens living in a periodontal pocket and hidden in plaque which is hard to remove are no exception, and it was shown that they are eradicated immediately or within 10 minutes by injection of the present bactericidal disinfectant, with some variation depending on the type and degree of growth of the plaque. Another point which should be mentioned regarding the action of "the bactericidal disinfectant is that not only is there virtually no damage to cells or tissue as shown in the animal and human experiments mentioned above, but it also promotes tissue regeneration.

Test Example 5

Approximately 1 cm² pieces of skin were detached from mice, and ordinary concentrations of the various bactericidal disinfectants contained in absorbent cotton were applied to the wounds twice a day, morning and night. Water was applied as a control. The results are as shown in Table 6: in the case of the control mice it took 5 days for a thin skin to be regenerated on the wound, 12 days for the skin to recover its original thickness, and 35 days for the coat to grow back, while when the present bactericidal disinfectant was applied, the wound closed in 4 days, the skin recovered its original thickness in 10 days and the coat grew back in only 30 days. These results are quite similar to those for iodine tincture, signifying that the present bactericidal disinfectant and iodine tincture promote tissue regeneration. By contrast, after application of Hibitane gel, 3% aqueous hydrogen peroxide and acrinol, which are widely used in dentistry, it took 5 days for thin skin to form, 12 to 15 days for the skin to recover its original thickness and 40 days for the coat to grow back. In other words, these disinfectants act as toxins to inhibit tissue regeneration.

TABLE 6

Recovery from skin damage using various bactericidal disinfectants

| | Recovery | | |
|---|---|---|---|
| | Thin skin overall | Skin with roughly original thickness | Complete recovery (coat grown back) |
| The bactericidal disinfectant | 4 days | 10 days | 30 days |
| Hibitane gel | 5 days | 12 days | 38 days |
| 3% aqueous hydrogen peroxide | 5 days | 15 days | 40 days |
| Acrinol | 5 days | 15 days | 40 days |
| Iodine tincture | 4 days | 10 days | 32 days |
| Water | 5 days | 12 days | 35 days |

Test Example 6

Red worms with a mean length of 40 mm were prepared in groups of 10, the annuli of the red worms were severed with a cutter, and ordinary concentrations of the various bactericidal disinfectants contained in absorbent cotton were applied to the severed ends twice a day, morning and night. Application to the ends was continued even after the severed ends healed, and recovery and growth were observed. Water was applied as a control. The results are as shown in Table 7, and the present bactericidal disinfectant promoted tissue regeneration and the death rate was low, while with widely-used bactericidal disinfectants the death rate was high, indicating that they are toxic to tissue and inhibit regeneration.

TABLE 7

Effects of various disinfectants on growth of severed red worms

| | Length when severed | Number of days after severing | | | | | | | Deaths |
|---|---|---|---|---|---|---|---|---|---|
| | | 5 | 10 | 15 | 20 | 30 | 40 | 50 | |
| The bactericidal disinfectant | 20 mm | 22 mm | 23 mm | 25 mm | 26 mm | 28 mm | 31 mm | 34 mm | 2 |
| Hibitane gel | 20 mm | 21 mm | 22 mm | 23 mm | — | — | — | — | 10 |
| 3% aqueous hydrogen peroxide | 20 mm | 21 mm | 22 mm | 23 mm | 24 mm | 25 mm | 27 mm | 28 mm | 7 |
| Acrinol | 20 mm | 21 mm | 22 mm | 23 mm | 24 mm | 27 mm | 29 mm | 30 mm | 8 |
| Iodine tincture | 20 mm | 21 mm | 22 mm | 23 mm | 25 mm | 28 mm | 30 mm | 32 mm | 3 |
| Water | 20 mm | 21 mm | 22 mm | 23 mm | 25 mm | 28 mm | 30 mm | 32 mm | 6 |

Test Example 7

Ordinary concentrations of the various bactericidal disinfectants contained in absorbent cotton were applied several times a day for 2 months to the bases of the thumbnails of the left hands of 6 of the volunteers, the lengths of the untreated thumbnails of the right hands were measured, and elongation was investigated. As a general rule the bacterial disinfectants were applied immediately after hand washing. Nail growth and shape are closely tied to individual physical condition, and are a benchmark of health. Consequently, looking at what phenomena were induced by application of bactericidal disinfectants, there were no particular changes in shape but there were differences in elongation rates. The results are as shown in Table 8, and nail elongation was 5 to 6% greater when the present bactericidal disinfectant was applied, but was suppressed by 5 to 6% when Hibitane gel or acrinol was applied. As in the aforementioned tests on mouse skins and red worms, this shows that the present bactericidal disinfectant promotes tissue regeneration, while Hibitane and acrinol suppress tissue regeneration. No significant differences in elongation were seen between the right and left hands when 3% aqueous hydrogen peroxide and iodine tincture were applied.

TABLE 8

Elongation (mm) of nails after application of various bactericidal disinfectants

| | Thumbnail (right/left) | Days elapsed | | | | | |
|---|---|---|---|---|---|---|---|
| | | 10 | 20 | 30 | 40 | 50 | 60 |
| This bactericidal disinfectant | Right | 0.9 | 1.8 | 2.7 | 3.7 | 4.6 | 5.5 |
| | Left | 0.9 | 1.9 | 2.8 | 3.8 | 4.8 | 5.8 |
| Hibitane gel | Right | 0.9 | 1.8 | 2.7 | 3.6 | 4.5 | 5.3 |
| | Left | 0.8 | 1.7 | 2.5 | 3.3 | 4.2 | 5.0 |
| 3% aqueous hydrogen peroxide | Right | 0.9 | 1.8 | 2.7 | 3.6 | 4.5 | 5.4 |
| | Left | 0.9 | 1.8 | 2.7 | 3.6 | 4.5 | 5.4 |
| Acrinol | Right | 0.8 | 1.7 | 2.6 | 3.5 | 4.3 | 5.2 |
| | Left | 0.8 | 1.6 | 2.4 | 3.3 | 4.0 | 4.8 |
| Iodine tincture | Right | 0.9 | 1.8 | 2.7 | 3.7 | 4.6 | 5.5 |
| | Left | 0.9 | 1.8 | 2.7 | 3.8 | 4.7 | 5.6 |
| Water | Right | 0.8 | 1.6 | 2.4 | 3.2 | 4.0 | 4.7 |
| | Left | 0.8 | 1.6 | 2.4 | 3.2 | 4.0 | 4.7 |

Test Example 8

As shown in Table 9, addition of a dilution of the present bactericidal disinfectant to medium stimulated growth of the Lactobacillus used in the present invention. It is well known that growth of Lactobacillus is promoted by addition of acetic acid, but it is surprising that a bactericidal disinfectant having bactericidal action should promote growth, even though diluted. However, as shown in Table 10, this effect does not apply to periodontal pathogens and other pathogenic bacteria. In other words this means that if that if the present bactericidal disinfectant is first injected into a periodontal pocket which is then lightly washed in water and filled with the novel Lactobacillus casei of the present invention (hereunder, "novel Lactobacillus" of the present invention) having specific properties as described below, the growth of the "novel Lactobacillus" will be promoted, and its therapeutic effects on periodontal disease will be enhanced. In the case of widely-used disinfectants, even when added to media at different concentrations, the growth of the bacteria might be suppressed but never stimulated. Moreover, the ferric ion ($Fe^{3+}$) which is the principal component of the present bactericidal disinfectant is adsorbed by the tooth surfaces, serving as a barrier to prevent re-adherence of periodontal pathogens. In addition, because it is astringent it temporarily reduces secretion of gingival sulcus fluid, which serves as a nutritional source for periodontal pathogens, thus suppressing the growth and proliferation of periodontal pathogens hidden inside by cutting off part of their nutritional source.

TABLE 9

Effect of the bactericidal disinfectant on growth of lactic acid bacteria

| | Dilution of ordinary concentration of this bactericidal disinfectant contained in medium | | | | | | |
|---|---|---|---|---|---|---|---|
| | 1/10 | 1/30 | 1/50 | 1/100 | 1/200 | 1/300 | 1/500 |
| "Novel Lactobacillus" (L. casei) | − | ± | + | ++ | + | + | ± |
| Other L. casei | − | − | ± | + | + | ± | ± |
| L. acidophilus | − | − | ± | + | + | ± | ± |
| L. pluntarum | − | − | + | + | + | ± | ± |
| L. burgaricus | − | − | ± | + | + | ± | ± |
| L. salivarius | − | − | + | + | + | ± | ± |
| L. fermentum | − | − | ± | + | + | ± | ± |

− Growth suppressed
± Growth neither suppressed nor promoted
+ Growth promoted

TABLE 10

Effect of the bactericidal disinfectant on growth of pathogenic bacteria

| | Dilution of ordinary concentration of this bactericidal disinfectant contained in medium | | | | | | |
|---|---|---|---|---|---|---|---|
| | 1/10 | 1/30 | 1/50 | 1/100 | 1/200 | 1/300 | 1/500 |
| P. gingivalis | − | − | ± | ± | ± | ± | ± |
| P. intermedia | − | − | ± | ± | ± | ± | ± |
| A. actino. | − | − | ± | ± | ± | ± | ± |
| S. aureus | − | − | ± | ± | ± | ± | ± |
| S. pyogenes | − | − | ± | ± | ± | ± | ± |
| E. coli O-157 | − | − | ± | ± | ± | ± | ± |
| S. enteritidis | − | − | ± | ± | ± | ± | ± |
| Ps. aeruginosa | − | − | ± | ± | ± | ± | ± |
| V. parahaemoliticus | − | − | ± | ± | ± | ± | ± |

− Growth suppressed
± Growth neither suppressed nor promoted
+ Growth promoted

In the present invention a preparation containing a novel *Lactobacillus casei* signifies both a preparation containing the "novel *Lactobacillus*" alone and a preparation containing the "novel *Lactobacillus*" and antibiotics, and either can be used for treating periodontal disease.

Test Example 9

It has been shown from animal tests that the toxicity of *P. gingivalis* and *P. intermedia* can be estimated in terms of quality and quantity of toxins produced by observing the hue and odor of a black colony on a blood plate and the strength of adhesion to the plate, while for *A. actinomycetemcomitans* the quality and quantity of toxins produced can be estimated by observing hemolytic strength and adhesiveness. Therefore, the aforementioned principal periodontal pathogens were cultured together with the "novel *Lactobacillus*" in order to see what tendencies and reactions the periodontal pathogens would exhibit. Modified GAM bouillon (Nissui Pharmaceutical Co.) was used as the medium, culture was performed anaerobically at 37° C. with subcultures every 72 hours, at which time a dilution was applied by ordinary methods to blood plate medium, and the cell numbers and condition of the emerging colonies were observed over time. The results are shown in Tables 11, 12 and 13. As shown in Table 11, cell numbers of *P. gingivalis* decreased gradually with each passage, disappearing by the $25^{th}$ passage. During that time toxicity weakened gradually after the $5^{th}$ passage, and was still slightly present by the $15^{th}$ passage but almost gone by the $20^{th}$. It was confirmed that no gingivitis occurred when periodontal locations of mice were infected with these bacteria. As shown in Table 12, cell numbers of *P. intermedia* decreased gradually with number of passages, disappearing by the $15^{th}$ passage. Pathogenicity weakened concomitantly, and was eliminated by the $12^{th}$ passage. Moreover, as shown in Table 13, cell numbers of *A. actinomycetemcomitans* also decreased with each passage, but not as rapidly as in the cases of *P. gingivalis* and *P. intermedia*. Past a certain point, however, they decreased rapidly and disappeared by the $18^{th}$ passage. In mouse experiments, pathogenicity disappeared completely by the $12^{th}$ passage. Similar co-culture experiments were performed for other bacteria associated with periodontal disease such as *F. nucleatum, B. forsythus, L. buccalis, E. corrodens* and *Streptococcus* bacteria common in the oral cavity, and it was shown that all of these were overcome by the reproductive force and bioactive substances of the *Lactobacillus* of the present invention, with cell numbers and toxicity decreasing rapidly with each passage.

TABLE 11

Results for co-culture of *P. gingivalis* and FERM P-19443

| | | *P. gingivalis* | | | | | |
|---|---|---|---|---|---|---|---|
| Passage number | FERM P-19443 | Cell number | % | Condition of colony | | | Changes in pathogenicity |
| | | | | Hue | Odor | Adhesiveness | |
| 1 | $1.8 \times 10^9$ | $2.2 \times 10^9$ | 55% | Black, luster | Strong putrefaction odor | Strong adhesiveness | Strong |
| 3 | $1.5 \times 10^9$ | $1.5 \times 10^9$ | 50% | Black, luster | Strong putrefaction odor | Strong adhesiveness | Moderate to strong |
| 5 | $1.8 \times 10^9$ | $5 \times 10^8$ | 22% | Blackish-brown | Moderate putrefaction odor | Moderate adhesiveness | Moderate |
| 10 | $2 \times 10^9$ | $2 \times 10^8$ | 10% | Brown | Weak putrefaction odor | Weak adhesiveness | Weak |
| 15 | $2.5 \times 10^9$ | $5 \times 10^7$ | 2% | Gray | Very weak putrefaction odor | Peels easily | Very weak |
| 20 | $3 \times 10^9$ | $1 \times 10^6$ | 0.3% | Whitish-gray | No odor | No adhesiveness | Almost none |
| 25 | $3 \times 10^9$ | 0 | 0% | | | | |

TABLE 12

Results for co-culture of *P. intermedia* and FERM P-19443

| Passage number | FERM P-19443 | Cell number | % | Hue | Odor | Adhesiveness | Changes in pathogenicity |
|---|---|---|---|---|---|---|---|
| | | *P. intermedia* | | | | | |
| 1 | $2.1 \times 10^9$ | $2 \times 10^9$ | 48% | Black | Putrefaction odor | Strong adhesiveness | Strong |
| 3 | $2.3 \times 10^9$ | $1 \times 10^9$ | 30% | Black | Putrefaction odor | Moderate adhesiveness | Modorate |
| 5 | $2.5 \times 10^9$ | $2 \times 10^8$ | 7.4% | Center brown | Weak putrefaction odor | Weak adhesiveness | Moderate to weak |
| 10 | $2.8 \times 10^9$ | $5 \times 10^7$ | 1.8% | Brown | Very weak putrefaction odor | Almost no adhesiveness | Very weak |
| 12 | $3 \times 10^9$ | $1 \times 10^7$ | 0.3% | Grayish-white | No odor | None | Almost none |
| 15 | $3 \times 10^9$ | 0 | 0% | | | | |

TABLE 13

Results for co-culture of *A. actinomycetemcomitans* and FERM P-19443

| Passage number | FERM P-19443 | Cell number | % | Hemolysis | Odor | Adhesiveness | Changes in pathogenicity |
|---|---|---|---|---|---|---|---|
| | | *P. Actinomycetemcomitans* | | | | | |
| 1 | $2 \times 10^9$ | $2.3 \times 10^9$ | 53% | Strong (extensive) | Putrefaction odor | Strong adhesiveness | Strong |
| 3 | $2.5 \times 10^9$ | $1.2 \times 10^9$ | 32% | Strong (extensive) | Putrefaction odor | Strong adhesiveness | Strong |
| 5 | $2.5 \times 10^9$ | $8 \times 10^8$ | 24% | Moderate | Moderate putrefaction odor | Moderate adhesiveness | Moderate |
| 10 | $2.5 \times 10^9$ | $2 \times 10^8$ | 7.4% | Weak (restricted) | Weak putrefaction odor | Weak adhesiveness | Weak |
| 12 | $2.8 \times 10^9$ | $1 \times 10^8$ | 3.4% | Weak (restricted) | Weak putrefaction odor | Weak adhesiveness | Eliminated |
| 15 | $3 \times 10^9$ | $3 \times 10^7$ | 1% | None | Very weak putrefaction odor | Almost no adhesiveness | Eliminated |
| 18 | $3 \times 10^9$ | 0 | 0% | | | | |

Test Example 10

When the "novel *Lactobacillus*" (FERM P-19443) was streak cultured anaerobically for 72 hours in the middle of a plate of diameter 90 mm and various periodontal pathogens were then streak cultured up to its edge, development of the periodontal pathogens was arrested near the growth locations of FERM P-19443 due to the effect of active substances such as antibiotics and the like produced by FERM P-19443. Next, periodontal pathogens growing on the edge where development was arrested were sampled and streak cultured on a new growth plate of FERM P-19443, and this step was repeated to observe changes in the zone of growth. In this test, FERM P-19443 and the periodontal pathogens were not mixed as they were in Test example 9. Modified GAM medium was used for the plates. The test results were as shown in FIG. 14: the zone of arrest due to FERM P-19443 remained approximately the same from the first passage up to a certain number of passages, but grew rapidly after that point, and by the $13^{th}$ to $15^{th}$ passage the pathogens were eliminated from the plate and disappeared. At the same time toxicity became gradually weaker and was finally eliminated.

TABLE 14

Effects of novel *Lactobacillus* (FERM P-19443 strain) on periodontal pathogens

| Periodontal pathogen | Changes in scope of arrest (mm) depending on number of passages | | | | | | | |
|---|---|---|---|---|---|---|---|---|
| | $1^{st}$ | $3^{rd}$ | $5^{th}$ | $7^{th}$ | $9^{th}$ | $11^{th}$ | $13^{th}$ | $15^{th}$ |
| P. gingivalis | 15 | 20 | 22 | 22 | 26 | 32 | 43> | |
| P. intermedia | 18 | 25 | 24 | 25 | 29 | 35 | 43> | |
| A. actinomycetemcomitans | 12 | 10 | 13 | 18 | 30 | 35 | 40 | 43> |
| F. nucleatum | 20 | 20 | 20 | 25 | 28 | 38 | 43> | |
| B. forsythus | 16 | 18 | 23 | 22 | 27 | 35 | 39 | 43> |

43> Streak cultured but did not grow

In sensitivity tests using known antibiotics, the zone of arrest shrank gradually with each passage without exception, and resistance was eventually achieved. In other words antibiotic-resistant strains emerged, and in most cases the toxicity of the pathogen was unchanged or grew stronger. It is well known that the emergence and spread of MRSA and other VREs, multiple drug resistant *Mycobacterium tuberculosis* and *Ps. aeruginosa* and the like is becoming a serious problem world-wide. It was confirmed from the tests of Test examples 9 and 10 above that the development and proliferation of periodontal pathogens is gradually suppressed by the powerful effects of FERM P-19443 whether it directly contacts them or not, without any resistant strains emerging, and that toxicity is completely eliminated.

Test Example 11

In order to measure the establishment of the "novel *Lactobacillus*" (FERM P-19443 strain) in the periodontal pocket, a suspension of bacteria ($2\times10^{10}$/ml) suspended in sterile saline was injected into a pocket of equivalent depth, sterile saline was injected into the pocket beginning the following day and left for 5 minutes, the injected saline was re-collected by suction, and the growth and decline of FERM P-19443 were observed every day for a week. The same cell numbers of *L. acidophilus*, which colonizes mucous membranes, and *B. natto*, which produces mucous and is highly adhesive, were injected separately as controls, and their progress observed. The results are as shown in Table 15, and it was confirmed that when $2\times10^{10}$/ml of FERM P-19443 is injected most of it flows out (90% to 95%), but the remaining bacteria are established for about a week and the establishment rate is greater the deeper the pocket. In other words, FERM P-19443 can grow with gingival sulcus fluid as its main nutritional source, and can be more active the more advanced the periodontal disease. In contrast, *L. acidophilus* was not observed from the fourth day on or *B. natto* from the third day on. That is, these bacteria cannot become established and proliferate in the periodontal pocket.

TABLE 15

| | | Growth and decline of bacteria injected into periodontal pocket | | | | | | | |
|---|---|---|---|---|---|---|---|---|---|
| Depth of periodontal pocket (mm) | 1 hour after injection | Growth and decline of injected bacteria (cell number/ml) | | | | | | | |
| | | 1 day | 2 days | 3 days | 4 days | 5 days | 6 days | 7 days | |
| FERM P-19443 | | | | | | | | | |
| 10 mm | $1 \times 10^9$ | $3 \times 10^8$ | $1 \times 10^8$ | $3 \times 10^7$ | $1 \times 10^7$ | $2 \times 10^6$ | $2 \times 10^4$ | 0 | |
| 15 mm | $1 \times 10^9$ | $5 \times 10^8$ | $1.5 \times 10^8$ | $8 \times 10^7$ | $3 \times 10^7$ | $4 \times 10^6$ | $3 \times 10^5$ | $3 \times 10^4$ | |
| 20 mm | $2 \times 10^9$ | $8 \times 10^8$ | $2 \times 10^8$ | $1 \times 10^8$ | $7 \times 10^7$ | $1 \times 10^7$ | $5 \times 10^6$ | $5 \times 10^5$ | |
| L. acidophilus | | | | | | | | | |
| 15 mm | $1 \times 10^9$ | $1 \times 10^8$ | $5 \times 10^6$ | $5 \times 10^3$ | 0 | 0 | 0 | 0 | |
| B. natto | | | | | | | | | |
| 10 mm | $5 \times 10^9$ | $5 \times 10^7$ | $3 \times 10^4$ | 0 | 0 | 0 | 0 | 0 | |

Test Example 12

The growth and decline of cell numbers were observed when the "novel *Lactobacillus*" (FERM P-19443) was administered by injection every day into the periodontal pocket and when it was administered by injection every other day. The results are as shown in Table 16, and it was shown that when the bacteria are administered every day cell numbers in the pocket increase gradually, with greater establishment and proliferation the deeper the pocket, while when administration is on alternate days establishment and proliferation are somewhat less than with daily injection but there is still a gradual increase overall. This suggested that it is sufficient to administer the bacteria by injection every other day.

gressed slowly, and ultimately almost 100% of them died. In the test group treated with the "novel *Lactobacillus*" (FERM P-19443), those with mild symptoms were almost completely cured regardless of the water temperature. When the symptoms were moderate the wounds gradually healed, and no goldfish died even after two months.

TABLE 16

Growth and decline of FERM P-19443 in periodontal pocket

| Depth of periodontal pocket (mm) | Growth and decline of FERM P-19443 (cell number/ml) | | | | | | |
|---|---|---|---|---|---|---|---|
| | 1 day | 2 days | 3 days | 4 days | 5 days | 6 days | 7 days |
| Daily administration | | | | | | | |
| 10 mm | $3.5 \times 10^8$ | $5 \times 10^8$ | $5 \times 10^8$ | $7 \times 10^8$ | $8 \times 10^8$ | $8 \times 10^8$ | $1 \times 10^9$ |
| 15 mm | $5 \times 10^8$ | $8 \times 10^8$ | $1 \times 10^9$ | $1.2 \times 10^9$ | $1.5 \times 10^9$ | $1.8 \times 10^9$ | $2 \times 10^9$ |
| 20 mm | $8.5 \times 10^8$ | $12 \times 10^9$ | $1.8 \times 10^9$ | $2.5 \times 10^9$ | $3.2 \times 10^9$ | $4 \times 10^9$ | $5 \times 10^9$ |
| Administration on alternate days | | | | | | | |
| 10 mm | $3 \times 10^8$ | $1 \times 10^8$ | $4 \times 10^8$ | $1.5 \times 10^8$ | $6 \times 10^8$ | $2 \times 10^8$ | $6.5 \times 10^8$ |
| 15 mm | $5 \times 10^8$ | $1 \times 10^8$ | $6.5 \times 10^8$ | $2 \times 10^8$ | $8 \times 10^8$ | $2.5 \times 10^8$ | $1.2 \times 10^9$ |
| 20 mm | $8 \times 10^8$ | $2 \times 10^8$ | $1 \times 10^9$ | $3 \times 10^8$ | $2 \times 10^9$ | $8 \times 10^8$ | $2.8 \times 10^9$ |

The "novel *Lactobacillus*" (FERM P-19443) is not only effective against a variety of acute and chronic infections, but it also shows effectiveness in improving systemic, chronic physical conditions such as diabetes which are aggravating factors in periodontal disease. In other words, administration of the novel *Lactobacillus* of the present invention enhances the body's natural healing power, resulting in greater vitality. Vitality is nothing more than the body's ability to promote growth and repair tissue. The results of several tests are presented here.

Test Example 13

Goldfish (Wakin) suffering from goldfish ulcer disease caused by *Aeromonas* which infect wounds and decompose surrounding muscle so that in severe cases the organs are exposed were separated into three groups, an untreated group, a control group and a test group, rearing water temperatures of 15° C., 20° C. and 25° C. were set for each group, and the goldfish were observed for 2 months in a total of 9 tanks. Five goldfish were reared in each of the tanks in 5 L of water. 1 g ($5 \times 10^6$ cells/ml tank water) of freeze-dried cells of *L. casei* standard strain ATCC 393 were administered to the control group and 1 g ($5 \times 10^6$ cells/ml tank water) of freeze-dried cells of the "novel *Lactobacillus*" (FERM P-19443) to the test group, each on alternate days. The untreated group was reared without any treatment. The symptoms of goldfish ulcer disease ranged from mild to moderate, and the groups were carefully balanced in each tank. The results are as shown in Table 17, and the symptoms of the untreated group progressed regardless of water temperature, and within 2 months all goldfish had exposed organs and died. In the control group which received *L. casei* standard strain ATCC 393, none of the goldfish with mild symptoms which were reared at a low water temperature died although their wounds did spread, but the symptoms of the goldfish reared in the other tanks pro-

TABLE 17

Therapeutic effects on goldfish ulcer disease

| Water temp. | Group | 1 month | 2 months | Death rate |
|---|---|---|---|---|
| 15° C. | Untreated | Even wounds of fish with mild symptoms spread gradually; 3 died | Even wounds of fish with mild symptoms spread; remaining 2 died | 100% |
| | Control | Wounds of fish with mild symptoms spread slightly; those of fish with moderate symptoms spread gradually | No fish with mild symptoms died although symptoms progressed; all with moderate symptoms died | 80% |
| | Test | Wounds of fish with mild symptoms mostly closed after 1 month; those of fish with moderate symptoms unchanged or slightly closed | Fish with mild symptoms completely healed; wounds of those with moderate symptoms no longer obvious | 0% |
| 20° C. | Untreated | Similar trend as at 15° C.; 1 fish with mild symptoms and 2 with moderate symptoms died | Similar progress as at 15° C.; remaining 2 fish died | 100% |
| | Control | Similar to results at 15° C. | Similar to results at 15° C. | 80% |
| | Test | Same progress as at 15° C. | Same progress as at 15° C. | 0% |
| 25° C. | Untreated | Wounds of even fish with mild symptoms spread rapidly; all died | | 100% |
| | Control | Wounds of even fish with mild symptoms grew deeper, and those of fish with moderate symptoms rapidly grew larger | All fish died within a month and a half | 100% |
| | Test | Fish with mild symptoms were unchanged; wounds of fish with moderate symptoms gradually shrank | Wounds of fish with mild symptoms no longer obvious; those of fish with moderate symptoms smaller in all but one case | 0% |

Test Example 14

Planaria were divided into three groups as in Test Example 13, the five in each group were each cut at the median line, and the speed of regeneration was measured. The rearing tanks were set to 20° C., with water for the untreated group and $1 \times 10^8$ cells/ml tank water of L. casei standard strain ATCC 393 and the "novel Lactobacillus" (FERM P-19443), respectively, for the bacterial groups, and the water and bacterial water were changed every day. Diatoms and yeast were given freely as feed. Regeneration from 50% weight at time of cutting to 100% original weight was observed over time and measured. The measurement results are as shown in FIG. 1, and complete regeneration took 12 days for the untreated group and L. casei standard strain ATCC 393 group, while for the "novel Lactobacillus" (FERM P-19443 strain) group it took only 9 days. In other words, regeneration speed (tissue repair) was 33% faster than in the other groups, indicating that tissue repair ability is greater.

Test Example 15

Figure 2:
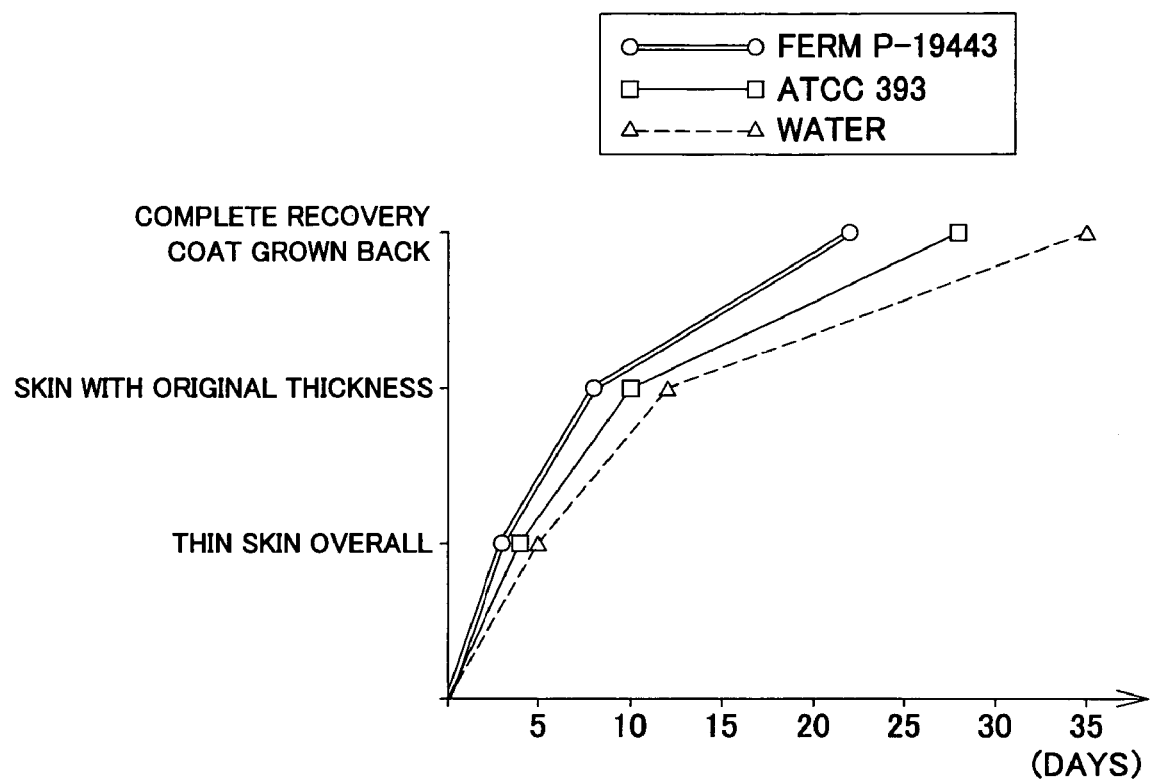
FIG. 2 shows regeneration of mouse skin after detachment.

Approximately 1 $cm^2$ pieces of skin were detached from mice, and water was then applied locally to the untreated group and centrifuged cells of L. casei standard strain ATCC 393 and the "novel Lactobacillus" (FERM P-19443) to the bacterial groups, twice a day morning and night, and the progress observed. The results of observation are as shown in FIG. 2: when FERM P-19443 was applied, it took only 3 days for a thin skin to form over the entire wound, 8 days for the skin to regenerate completely and only 22 days for the coat to grow back completely. By contrast, 4, 10 and 28 days respectively were required when ATCC 393 was applied, and 5, 12 and 35 days respectively when water was applied. The superior tissue repair ability of the "novel Lactobacillus" (FERM P-19443) appeared once again in this test.

Test Example 16

Figure 3:
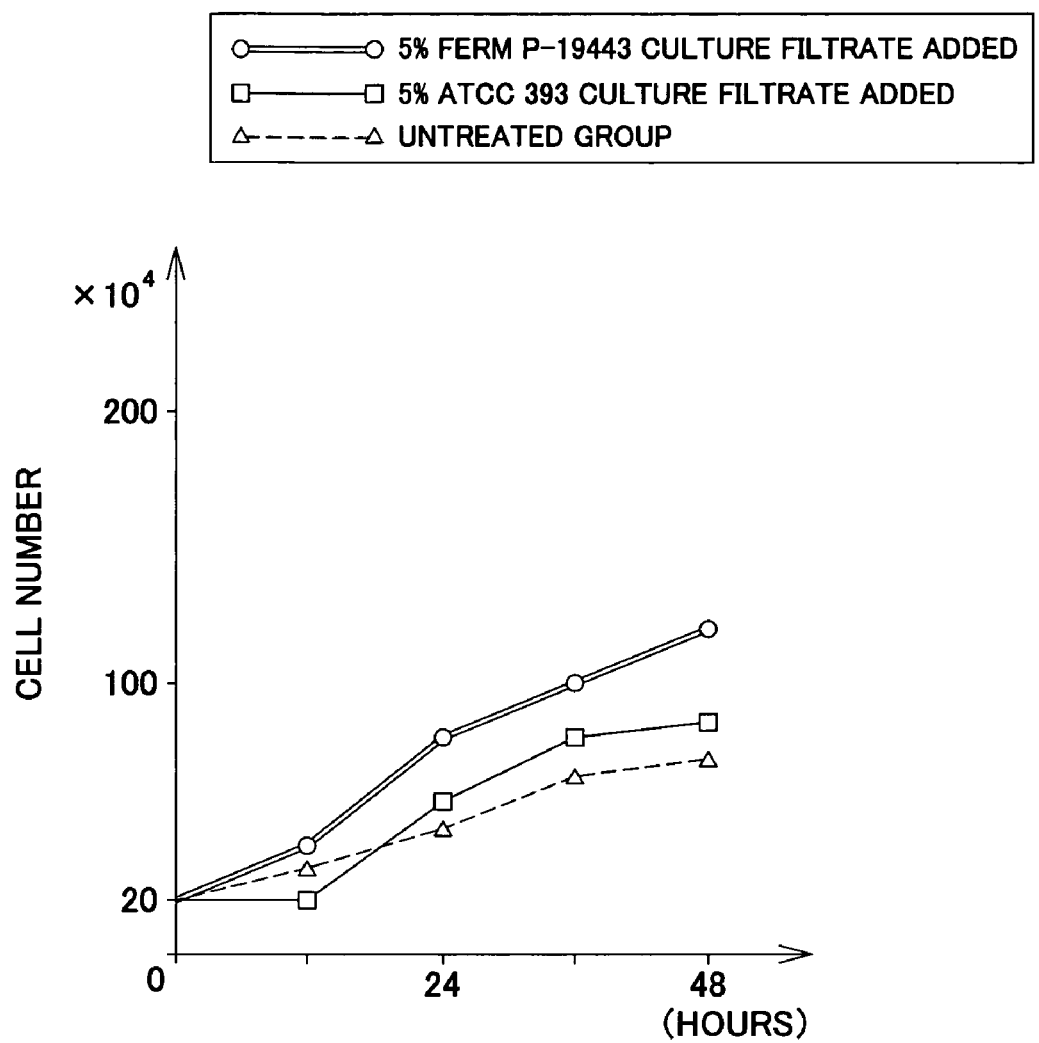
FIG. 3 shows proliferation of monkey kidney V-1 cell strain.
Figure 4:
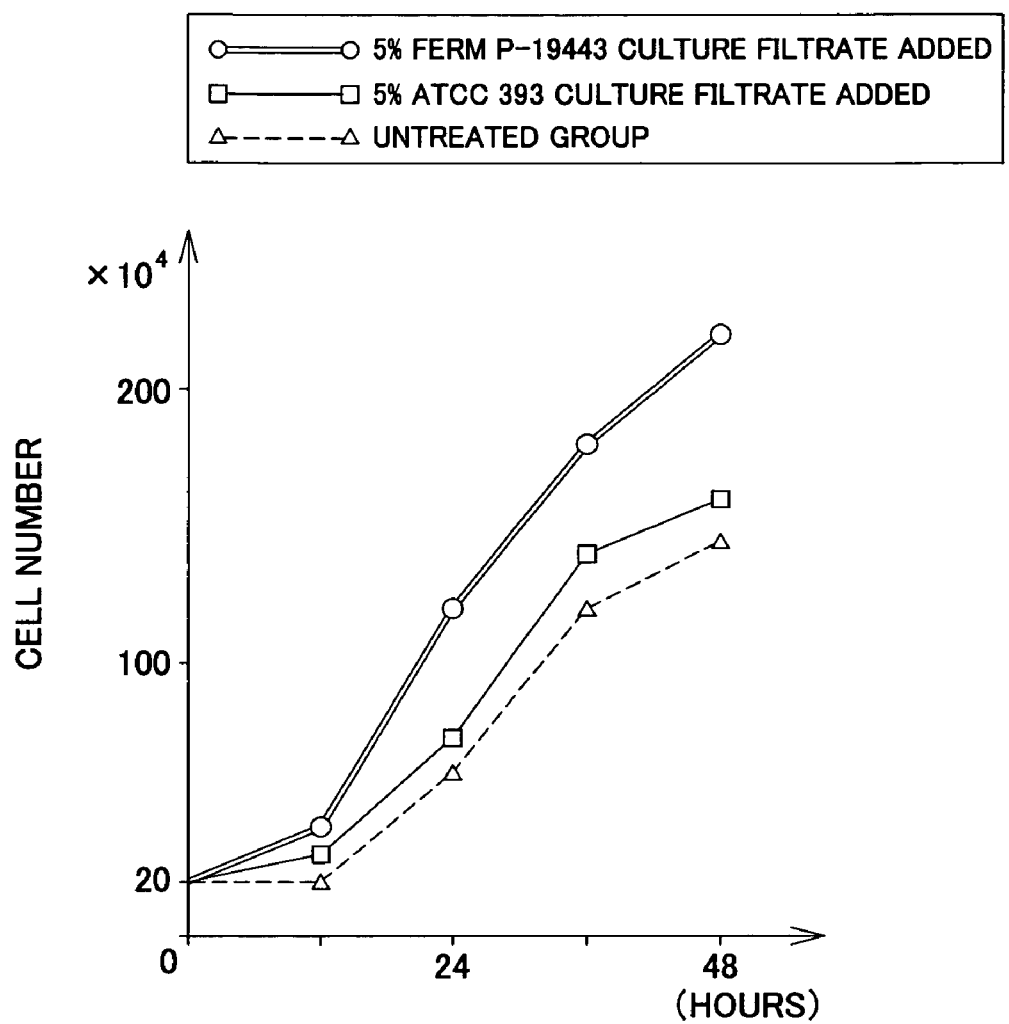
FIG. 4 shows proliferation of mouse mastocytoma cell strain P815.
Figure 5:
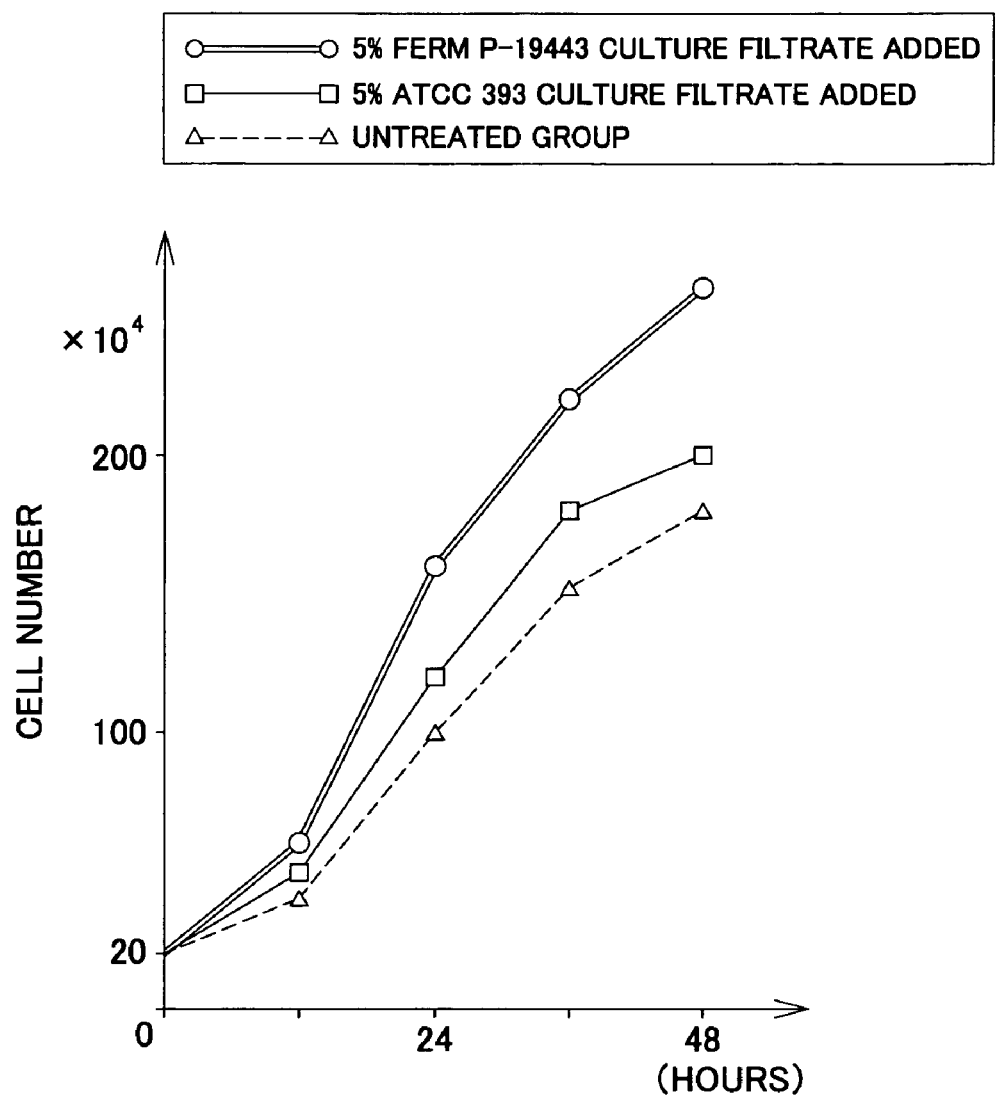
FIG. 5 shows proliferation of mouse lymphocyte CEA.
Figure 6:
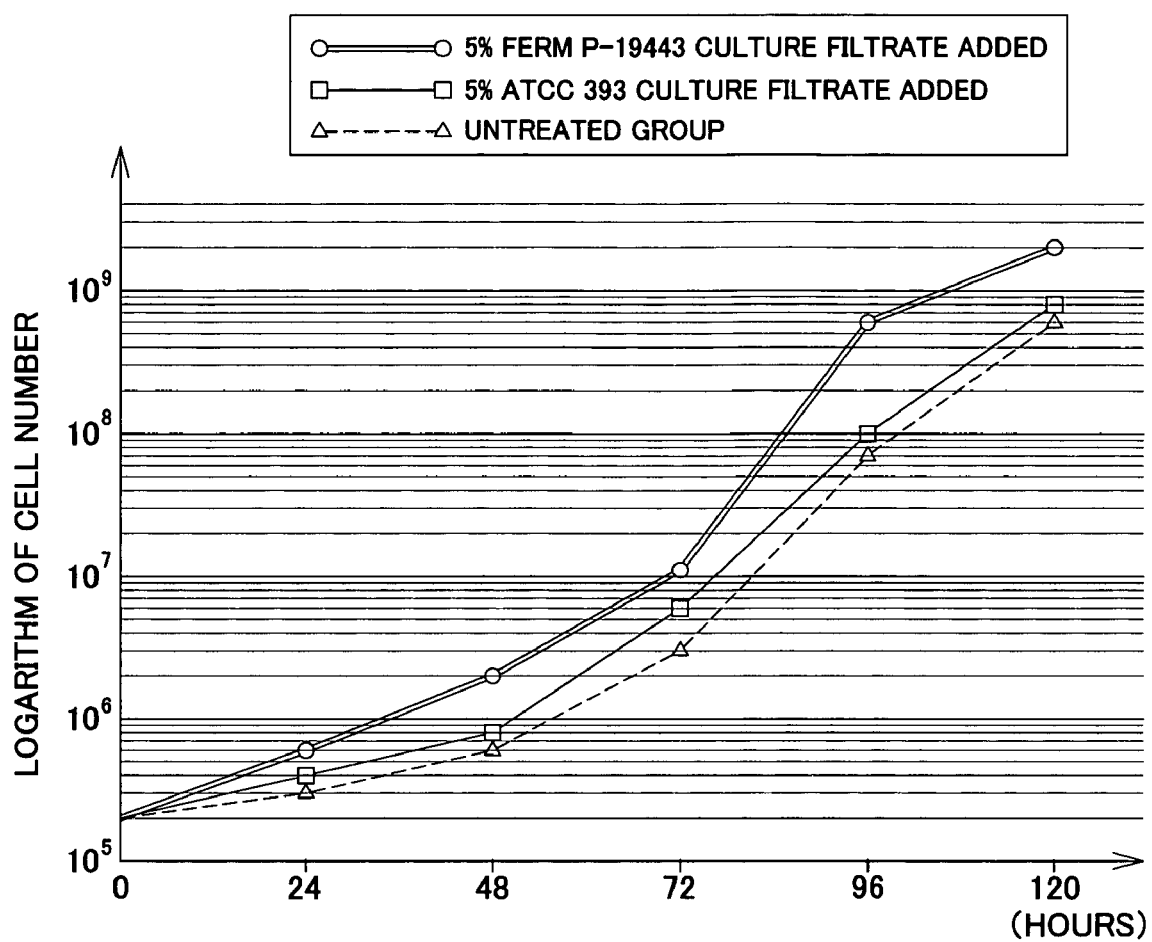
FIG. 6 shows proliferation of *chlorella*.

In order to investigate cell proliferation properties with respect to animal and plant cells, L. casei standard strain ATCC 393 and the "novel Lactobacillus" (FERM P-19443) were seeded on medium of pH 7.2 containing 3 g pepton, 2 g tripton, 3 g meat extract, 1 g CGF, 1 g yeast extract, 3 g starch, 1 g trehalose, 1.5 g $KH_2PO_4$, 0.7 g $MgSO_4.7H_2O$, 1 g NaCl, 1 g diammonium citrate, 1 g $(NH_4)_2HPO_4$, 2 g sodium acetate, 2 g $CaCO_3$, 0.2 g $MnSO_4.\chi H_2O$, 0.03 g $FeSO_4.7H_2O$, 0.01 g $ZnSO_4$, 0.2 g L-cystine and 1 g taurine per 1 L, and cultured anaerobically for 72 hours at 37° C. Monkey kidneys (V-1 cell strain), mouse mastocytoma cell strain P815 and mouse lymphocytes CEA were each mixed $2 \times 10^5$ cells/ml with culture liquids having 5% by volume of the centrifuged supernatant thereof added or not added to Nissui Pharmaceutical Co. animal cell culture GIT medium, and viable cell numbers were calculated after 48 hours. The results are shown in FIGS. 3, 4 and 5. As shown in the respective figures, animal cells were more proliferative when 5% by volume of Lactobacillus culture filtrate was added to their cell culture liquid, with an increase of 40% to 50% with FERM P-19443 in contrast to 10% to 15% for standard strain ATCC 393. This indicates that the products (bioactive substances) of Lactobacilli stimulate and promote proliferation (division) of animal cells, suggesting that increased proliferation of lymphocytes contributes to strengthening the immune system. Promotion of cell proliferation was also confirmed in a similar experiment performed with plant cells, although not to the degree that it was in animal cells.

The pathogenic factors of periodontal pathogens are various, including attachment-related factors, proteases and toxins as well as substances which affect toxicity and metabolic products which inflict direct or indirect damage on periodontal tissue. More specifically these include endotoxin (LPS1), collagenase, trypsin-like enzymes, fibroblast repressible enzymes and other disrupting enzymes, and leukocyte disrupting enzymes (leukotoxins), streptolysin, hydrogen sulfide, fatty acids and other cytotoxins, as well as adhesiveness by long cilia to mucous membrane epithelium, red blood cells and other bacteria. The effects of endotoxin in particular are various, including activation of osteoclasts (promoting absorption of alveolar bone), damage to fibroblasts, promotion of immunopathological reactions (causing tissue damage by over-stimulation of immune cells), Shwartzman reaction (circulatory damage to periodontal tissue) and the like. The "novel Lactobacillus" (FERM P-19443) not only arrests the proliferation of periodontal pathogens and weakens their pathogenicity, but can also break down and detoxify some of the toxins produced by the periodontal pathogens.

Test Example 17

Periodontal pathogens cultured anaerobically for 120 hours at 37° C. in modified GAM bouillon were collected by centrifugation, floated in saline and washed centrifugally in triplicate. They were next floated uniformly in 5 times the volume of water, cooled to 0° C., and left for 3 hours at 0° C. after addition of the same quantity of ice-cold 0.5 N trichloroacetic acid aqueous solution. Next the bacterial residue was removed by centrifugation, 2 parts of chilled ethanol were added to the supernatant, and the precipitate was centrifuged. The precipitate was washed with a small amount of ethanol and then with ether to obtain white, powdered endotoxin. A disc was permeated with 5 mg of this endotoxin and dried to prepare a sensitivity disc. Next, previously prepared sensitivity discs were placed in the middle of media consisting of L. casei standard strain ATCC 393 and the "novel Lactobacillus" (FERM P-19433) coated on BCP plate medium containing 2.5 g yeast extract, 5 g pepton, 1 g glucose, 0.1 g L-cystine, 1 g polysorbate 80 and 0.06 g BCP per 1 L, and culture was performed anaerobically for 48 hours at 37° C. As a result, even though growth of ATCC 393 was arrested within 12 mm of the edge of the disc, FERM P-19433 grew so that the edge of the disc was raised up. This shows that FERM P-19443 takes in this endotoxin as though it were a growth factor such as a vitamin. Moreover, the "novel Lactobacillus" (FERM P-19443) has the ability to actively reduce fatty acids and odorous sulfur compounds such as hydrogen sulfide, and proliferation is stimulated by addition of these substances.

Unfortunately, the treatment time was long and a complete cure was not achieved by merely administering FERM P-19443 either alone or together with antibiotics in cases of advanced periodontal disease. However, it was possible to prepare the groundwork for a cure by first applying the present bactericidal disinfectant. Namely, by removing the periodontal pathogens, preventing their re-adherence, promoting tissue regeneration and creating a strong support system for the free activity of FERM P-19443, and then rapidly removing toxins and other causal factors, it was possible to awaken the self-healing force which recognizes the teeth as self instead of rejecting them, and to upset the once-prevalent doctrine that periodontal disease is impossible to cure and maintaining the status quo is sufficient.

Working Examples

Next, the present invention is explained in detail based on manufacturing examples and working examples.

Manufacturing Example 1

For the bactericidal disinfectant of the present invention, an aqueous solution of 3,000 ppm ferric chloride hexahydrate as ferric ion ($Fe^{3+}$), an aqueous solution of 3,000 ppm L-ascorbic acid and an aqueous solution of 1,500 ppm potassium sorbate were prepared and mixed in equal amounts to manufacture the bactericidal disinfectant of the present invention.

Manufacturing Example 2

Sodium lauryl sulfate was added to a concentration of 100 ppm to the bactericidal disinfectant manufactured in Manufacturing Example 1, to manufacture the bactericidal disinfectant of the present invention.

Manufacturing Example 3

Tea tree oil was added to a concentration of 50 ppm to the bactericidal disinfectant manufactured in Manufacturing Example 1, to manufacture the bactericidal disinfectant of the present invention.

Manufacturing Example 4

For the novel Lactobacillus (FERM P-19443) preparation of the present invention the antibiotic-resistant novel Lactobacillus (FERM P-19443) of the present invention was seeded on 10 L of medium of pH 7.2 containing 5 g pepton, 3 g meat extract, 2 g yeast extract, 1 g CGF, 5 g starch, 1 g lactose, 2 g diammonium citrate, 3 g sodium acetate, 0.2 g $MgSO_4.7H_2O$, 0.03 g $FeSO_4.7H_2O$ and 1 g L-cystine per 1 L, and cultured anaerobically for 3 days at 37° C. After completion of culture, the culture liquid was paper filtered and centrifuged after removal of $CaCO_3$, and 7.8 g of the resulting cells was dispersed in 370 ml of saline and further centrifuged twice. The resulting clean bacterial mass was dispersed in 450 ml of pre-sterilized 5% starch solution, and vacuum freeze-dried by ordinary methods to obtain 30 g of novel Lactobacillus preparation. The live cell content of the bacterial preparation was $1 \times 10^{11}$ cells/g.

Manufacturing Example 5

The clean bacterial mass manufactured in Manufacturing Example 4 was mixed with 15.7 ml olive oil to manufacture an oil preparation which was refrigerated. The live cell content of this bacterial preparation was $2 \times 10^{11}$ cells/g.

Manufacturing Example 6

10 g of the oil preparation manufactured in Manufacturing Example 5 was mixed with 10 g hydrophilic ointment to manufacture a Lactobacillus cream. The live cell content of this bacterial preparation was $1 \times 10^{11}$ cells/g.

Manufacturing Example 7

400 mg of amoxicillin (AMPC), 100 mg of erythromycin (EM), 100 mg of fradiomycin (FRM) and 100 mg of cefaclor (CCL) as antibiotics were mixed with the Lactobacillus cream manufactured in Manufacturing Example 6, to manufacture a Lactobacillus cream containing antibiotics.

Since the progress of periodontal disease is mainly proportional to the depth of the pocket, it was classified into shallow periodontal disease in which pocket depth is 7 mm or less, moderate periodontal disease in which pocket depth is 7 to 15 mm and deep periodontal disease in which pocket depth is 15 mm or more. In end-stage periodontal disease, inflammation reaches the deepest part of the pocket, periodontal tissue is destroyed, most of the alveolar bone disintegrates, the tooth roots are exposed, the teeth are very loose because they cannot be supported and it is only a matter of time before they fall out. Consequently, treatment examples for periodontal disease are presented which employ the bactericidal disinfectant of the present invention (the present bactericidal disinfectant) and the novel Lactobacillus of the present invention (FERM P-19443) according to the progress of periodontal disease in the individual patient. The novel Lactobacillus preparations of the present invention are divided into a preparation containing only Lactobacillus as the principal ingredient (hereunder, "novel Lactobacillus preparation") and a preparation containing antibiotics (hereunder, "novel Lactobacillus preparation containing antibiotics"). A group using the present bactericidal disinfectant alone, a group using "novel Lactobacillus preparation containing antibiotics" alone and groups using the conventional widely-used disinfectants acrinol, Hibitane gel, 3% aqueous hydrogen peroxide and the like and an antibiotic (minocycline) were set up as comparative examples, excluding cases with end-stage symptoms. For the cases with end-stage symptoms, a method called "guided tissue regeneration" was adopted as the comparative example.

The basic operations adopted for the therapeutic method were to remove as much as possible of the plaque and calculus from all patients (scaling, root planing) and then either inject the present bactericidal disinfectant into the periodontal pocket or else wash the periodontal pocket thoroughly with the present bactericidal disinfectant leave it for 5 to 10 minutes, then rinse it lightly with water and immediately fill it with the "novel Lactobacillus preparation" or the "novel Lactobacillus preparation containing antibiotics." The "novel Lactobacillus" has acquired resistance to 16 types of widely-used antibiotics, and since a content of 20 mg amoxicillin, 5 mg erythromycin (EM), 5 mg fradiomycin (FRM) and 5 mg cefaclor (CCL) per gram of ointment and $1 \times 10^{11}$ cells/g ointment of the "novel Lactobacillus" was confirmed to have high effectiveness against periodontal pathogens and ordinary pathogenic bacteria, these proportions were adopted for the "novel Lactobacillus preparation containing antibiotics."

Example 1

5 patients with shallow periodontal disease were treated by first disinfecting the affected parts with the present bactericidal disinfectant and then injecting the "novel Lactobacillus preparation" into the affected parts. The results are shown in Table 18.

TABLE 18

Therapeutic effects of the therapeutic method of the present invention on shallow periodontal disease ("novel Lactobacillus preparation" used as Lactobacillus preparation)

| Patient | | | | Principal | |
|---|---|---|---|---|---|
| Name | Age | Sex | Site | pathogens | Therapeutic progress and results |
| T.K. | 58 | M | ⌐3 5⌐ | P. gingivalis B. forsythus | Gradual improvement from day 3 of administration, gum swelling and hue considerably improved by day 7, gums mostly closed by day 20, mostly cured by day 30 |
| K.M. | 54 | F | ⌐4 | P. gingivalis F. nucleatum | No halitosis by day 2, pathogens eradicated by day 5, gum swelling gone by day 7, pocket mostly closed by day 15, completely cured by day 30 |
| T.M. | 48 | M | ⌐2 6⌐ | P. gingivalis | Swelling receded by day after administration, gum hue and elasticity restored by day 3. Gum in pocket risen to close pocket by day 10. Mostly cured by day 25 |
| S.Y. | 70 | M | ⌐5 | P. intermedia S. aureus | Gradually improvement, halitosis better from about day 5. Gums had some elasticity by day 10, pocket somewhat closed by day 21, mostly closed by day 30 |
| H.K. | 36 | F | ⌐3 3⌐ | A. actino. S. aureus | Pathogens eliminated by day 3, pocket much shallower by day 7, mostly closed by day 15. Gum condition improved, mostly cured by day 25. |

Example 2

Five patients with shallow periodontal disease were treated by first disinfecting the affected parts with the present bactericidal disinfectant and then injecting the "novel *Lactobacillus* preparation containing antibiotics" into the affected parts. The results are shown in Table 19.

TABLE 19

Therapeutic effects of the therapeutic method of the present invention on shallow periodontal disease ("novel Lactobacillus preparation containing antibiotics" used as Lactobacillus preparation)

| Patient | | | | Principal | |
|---|---|---|---|---|---|
| Name | Age | Sex | Site | pathogens | Therapeutic progress and results |
| O.N. | 39 | M | ⌐6 7⌐ | P. gingivalis C. rectus | Swelling receded and halitosis gone by day 2. Pathogens gone by day 3, gum hue and elasticity restored by day 7, pocket shallower by day 10, mostly closed by day 15. |
| S.N. | 56 | F | ⌐4 5⌐ | A. actino. | Gradual improvement from day 3, gum condition mostly recovered by day 5, pocket somewhat shallower, mostly closed by day 12, mostly cured by day 20. |
| H.M. | 65 | F | ⌐4 3⌐ | A. actino. S. aureus | Improvement from day 5, rapid improvement from day 10, gum elasticity, hue, swelling mainly gone, gum risen in pocket, mostly closed by day 18 |
| I.T. | 67 | M | ⌐6 | P. intermedia A. actino. | Pathogens and halitosis eliminated by day after administration, slight drainage gone by day 3, gum in pocket risen by day 15, mostly closed by day 25, complete recovery |
| M.M. | 62 | M | ⌐5 6⌐ | P. gingivalis B. forsythus | Rapid improvement from about day 3, gum hue and elasticity restored by day 5, pocket shallower, closed and completely healed by day 20 |

Comparative Example 1

As comparative examples, five shallow periodontal disease patients each were treated with the present bactericidal disinfectant the "novel *Lactobacillus* preparation," the "novel *Lactobacillus* preparation containing antibiotics" and a conventional treatment method. The results are shown in Table 20.

TABLE 20

Results of treatment of shallow periodontal disease by conventional treatment methods

| | Average treatment progress and results for 5 patients |
|---|---|
| the present bactericidal disinfectant used alone | Pathogens eradicated by day 3, but gum swelling, hue, elasticity recovered only slightly. Periodontal pocket grew shallower but didn't close completely. No cure even after 2 months |
| "Novel *Lactobacillus* preparation" used alone | Gradual improvement several days after administration, halitosis gone. Gum hue, swelling, elasticity much better by day 15. Periodontal pocket mostly closed by day 30, mostly cured by day 60. |
| Conventional treatment method | Swelling receded by day 15 after beginning treatment, but swelling, elasticity still unsatisfactory. Pocket somewhat shallower by day 30, but didn't close with continued treatment. Gum hue and elasticity recovered. |
| "Novel *Lactobacillus* preparation containing antibiotics" used alone | Gradual improvement beginning several days after administration, gum hue, elasticity, swelling much improved by day 10. Gum pocket shallower by day 21, gums risen by day 30, mostly closed by day 45 |

When periodontal disease was limited to shallow areas, gum hue, swelling and elasticity recovered after 2 to 3 weeks' treatment by conventional treatment methods, but while the pocket grew shallower it never closed. By contrast, rapid improvement was seen immediately after commencement of treatment when the therapeutic method of the present invention was adopted, swelling receded rapidly, and within about 2 weeks gum hue and elasticity were mostly restored and the pocket became gradually shallower, closing completely within about a month for a complete cure.

Example 3

Five patients with moderate periodontal disease were treated by first disinfecting the affected parts with the present bactericidal disinfectant and then injecting the "novel *Lactobacillus* preparation" into the affected parts. The results are shown in Table 21.

TABLE 21

Therapeutic effects of the treatment method of the present invention on moderate periodontal disease ("novel Lactobacillus preparation" used as Lactobacillus preparation)

| Patient | | | | Principal | |
|---|---|---|---|---|---|
| Name | Age | Sex | Site | pathogens | Therapeutic progress and results |
| K.Y. | 50 | F | ⌊2  6⌉ | *P. intermedia* *Str. pyogenes* | Improving trend from day 5. Halitosis and pathogens eliminated, gum swelling gone and hue and elasticity restored by day 15. Pocket gradually grew shallower, mostly closed by day 45. Cured by day 60. |
| O.K. | 75 | F | ⌊2  2⌉ | *P. gingivalis* *Fusobacterium* | Gradual improvement from day 10 of administration, halitosis gone. Gum swelling, elasticity, hue much better by day 20. Gum in pocket risen slightly, much shallower by day 60. Mostly closed by day 90. |
| Y.T. | 68 | M | ⌊4  5⌉ | *P. gingivalis* *B. forsythus* | Discharged stopped and halitosis and pathogens eliminated by day 5. Gum hue, elasticity much better by day 10, pocket somewhat shallower. Gum tighter by day 20, mainly closed by day 35. |
| W.S. | 60 | M | ⌊2  4⌉ | *P. gingivalis* | Rapid improvement after day 7, gums tighter, discharge, bleeding, halitosis gone. Pocket shallower, mostly closed by day 21, complete cure. |
| T.T. | 44 | M | ⌊3  3⌉ | *A. actino.* *P. intermedia* | Gradual improvement after day 5, gum elasticity beginning to appear by day 10, hue pink by day 15, pocket gradually shallower, mostly closed by day 42. |

Example 4

Five patients with moderate periodontal disease were treated by first disinfecting the affected parts with the present bactericidal disinfectant and then injecting the "novel *Lactobacillus* preparation containing antibiotics" into the affected parts. The results are shown in Table 22.

TABLE 22

Therapeutic effects of the treatment method of the present invention on moderate periodontal disease ("novel Lactobacillus preparation containing antibiotics" used as Lactobacillus preparation)

| Patient Name | Age | Sex | Site | Principal pathogens | Therapeutic progress and results |
|---|---|---|---|---|---|
| U.M. | 36 | M | \|2\|3\|5̄ | P. gingivalis S. aureus | Improving trend from day 3, halitosis, pathogens, swelling eliminated. Gum hue, elasticity restored by day 12. Bleeding, discharged stopped by day 5. Pocket gradually shallower after day 15, mostly closed by day 35. |
| E.J. | 55 | F | \|5 | P. intermedia A. actino. | Rapid improvement after day 7, halitosis, bleeding, discharge eliminated. Gum hue, elasticity, swelling recovered by day 14, gum in pocket risen, completely closed by day 40. |
| K.I. | 65 | F | 3̄ \|2 | Fusobacterium E. corrodens | Improvement from day after administration, halitosis, bleeding, discharge gone by day 3, gums mainly recovered by day 7. Pocket gradually shallower, mostly closed by day 35 |
| S.S. | 72 | F | 4̄ 5̄ | W. recta B. forsythus | Rapid improvement from day 5, gum condition mostly cured by day 10. Gum in pocket still not risen satisfactorily. Took 48 days to close completely. |
| H.M. | 59 | M | \|6 \|5 | P. gingivalis | Halitosis, pathogens gone by day 3. Discharge, bleeding stopped by day 7. Gum condition gradually improved after day 15, mainly cured by day 28. Pocket never closed completely but mostly cured. |

Comparative Example 2

As comparative examples, five moderate periodontal disease patients each were treated with the present bactericidal disinfectant the "novel *Lactobacillus* preparation," the "novel *Lactobacillus* preparation containing antibiotics" and a conventional treatment method. The results are shown in Table 23.

TABLE 23

Results of treatment of moderate periodontal disease by conventional treatment methods

| | Average treatment progress and results for 5 patients |
|---|---|
| the present bactericidal disinfectant used alone | Pathogens eradicated by day 3, discharge, bleeding gone by day 5, gum swelling, hue, elasticity improved although gradually, pocket slightly shallower but did not close |
| "Novel *Lactobacillus* preparation" used alone | Pathogens gone by day 3, halitosis, discharge, bleeding subsided from day 5 while gum hue, swelling, elasticity also improved gradually. Pocket gradually shallower, mostly closed after 3 months but never closed completely |
| Conventional treatment method | Swelling receded by day 15 after beginning treatment, but swelling, elasticity almost unchanged. Pocket depth somewhat shallower but little difference. Status quo best that could be achieved. |
| "Novel *Lactobacillus* preparation containing antibiotics" used alone | Began to improve from day 10, halitosis, pathogens gone by day 15. Gum hue improving by day 30, elasticity also improved. Gum pocket somewhat shallower, but did not close completely even with continued treatment. |

When periodontal disease is moderate, swelling is reduced by conventional therapeutic methods, but hue and elasticity are still unsatisfactory, and while the pocket shrinks somewhat the change is not great. By contrast, using the therapeutic method of the present invention the pace of healing is slower than in the shallow cases, but improvement is steady and an almost complete cure is achieved in 2 to 3 months.

Example 5

Five patients with deep periodontal disease were treated by first disinfecting the affected parts with the present bactericidal disinfectant and then injecting the "novel *Lactobacillus* preparation" into the affected parts. The results are shown in Table 24.

TABLE 24

Therapeutic effects of treatment method of the present invention on deep periodontal disease ("novel Lactobacillus preparation" used as Lactobacillus preparation)

| Patient | | | | Principal | |
|---|---|---|---|---|---|
| Name | Age | Sex | Site | pathogens | Therapeutic progress and results |
| W.I. | 54 | F | ⌊6  ⌋2 | P. gingivalis<br>E. corrodens | Halitosis, pathogens gone by day 3. Bleeding, discharge improved by day 7. Gum condition improved, swelling and elasticity improving by day 15. Gum in pocket rising gradually, pocket shallower. |
| M.N. | 64 | M | ⌈5  ⌈6 | P. intermedia | Rapid improvement from day 5, bleeding, discharge gone by day 10. Gum condition improved, elasticity restored by day 30, gum in pocket beginning to rise, shallower by day 45, mostly closed by day 60. |
| N.M. | 70 | F | ⌊3  ⌊4 | A. actino.<br>P. intermedia | Gradually improvement from about day 7, halitosis, bleeding, discharge gone by day 15. Gum hue, swelling, elasticity began to improve rapidly after day 30, pocket began to shrink bit by bit, complete cure expected with continued treatment. |
| O.S. | 42 | M | 2⌋  ⌊5 | P. gingivalis | Gradual improvement from about day 5 of administration, bleeding, discharge, swelling gone by day 7. Gum condition began to improve, hue, elasticity recovered by day 20. Gum pocket also gradually shallower, mostly closed by day 60. |
| S.I. | 48 | M | ⌈6  3⌋ | P. gingivalis<br>B. forsythus | Halitosis, pathogens gone by day 3 of administration. Swelling receded by day 7. Bleeding, discharge stopped, gum hue, elasticity mainly restored by day 15. Gum in pocket risen slightly, shallower by day 45, mostly closed by day 65. |

Example 6

Five patients with deep periodontal disease were treated by first disinfecting the affected parts with the present bactericidal disinfectant and then injecting the "novel *Lactobacillus* preparation containing antibiotics" into the affected parts. The results are shown in Table 25.

TABLE 25

Therapeutic effects of the treatment method of the present invention on deep periodontal disease ("novel Lactobacillus preparation containing antibiotics" used as Lactobacillus preparation)

| Patient | | | | Principal | |
|---|---|---|---|---|---|
| Name | Age | Sex | Site | pathogens | Therapeutic progress and results |
| U.M. | 77 | M | ⌈3 ⌈4 ⌈5 | P. intermedia<br>P. gingivalis | Pathogens gone by day 3 of administration, bleeding, discharge gone by day 5. Gums began to improve from day 12, elasticity also recovered. Pockets gradually shallower, mostly closed by day 50. |
| T.K. | 80 | F | ⌊4 ⌊5 ⌊6 | P. gingivalis<br>S. aureus<br>S. pyogenes | Halitosis, pathogens gone by day 3 of administration. Bleeding, discharge gone, swelling better by day 7. Gum elasticity improved from day 15, hue also recovered. Gum in pocket rose slightly, pocket shallower but did not close |
| A.S. | 65 | F | ⌈2  ⌊4 | P. gingivalis<br>Fusobacterium | Recovery trend from day 4. Bleeding, discharge gone by day 7. Gum condition (hue, elasticity) mainly recovered from around day 15. Pocket gradually shallower, mostly closed by day 60. |
| S.A. | 47 | M | 6⌋  ⌊3 | A. actino.<br>Fusobacterium | Halitosis, pathogens gone by day 3, swelling improved by day 5, hue, elasticity mainly recovered by day 15. Periodontal pocket rapidly shallower, to a few mm by day 30, virtually closed by day 50. |
| T.T. | 50 | M | ⌈5  ⌈5 | P. intermedia<br>B. forsythus | Halitosis, pathogens gone by day 3, bleeding, discharge gone by day 5. Gum hue, elasticity better by day 15, completely recovered by day 30. Pocket gradually shallower, almost closed by day 60. |

Comparative Example 3

As comparative examples, five deep periodontal disease patients each were treated with, the "novel *Lactobacillus* preparation," the "novel *Lactobacillus* preparation containing antibiotics" and a conventional treatment method. The results are shown in Table 26.

TABLE 26

Results of treatment of deep periodontal disease by conventional treatment methods

| | Average treatment progress and results for 5 patients |
|---|---|
| the present bactericidal disinfectant used alone | Pathogens and halitosis eliminated after several days, gum swelling, hue, elasticity improved bit by bit, but not satisfactorily. Pocket depth changed little but felt somewhat shallower. |
| "Novel *Lactobacillus* preparation" used alone | Pathogen eliminated after 5 to 7 days, symptoms milder from about day 7, bleeding, discharge improved by day 10. Swelling receded gradually from about day 15, gums tightened. Hue improved, gum in pocket rose slightly, shallower but no complete cure |
| Conventional treatment method | Almost no improvement, barely maintained status quo. Gum swelling and elasticity improved slightly. Halitosis also improved. |
| "Novel *Lactobacillus* preparation containing antibiotics" used alone | Pathogens eliminated by day 5. Symptoms began to improve at the same time, bleeding and discharge gone. Gum condition improved from day 15, mainly recovered by day 25. Pocket grew shallower bit by bit but did not close. |

When the inflammation is deep, gum condition including swelling, hue, elasticity and the like improves slightly with the conventional method, but pocket condition remains virtually unchanged, and the status quo is barely maintained. By contrast, using the treatment method of the present invention there are individual differences, but gum condition begins to improve from about the second week of treatment, and a mainly health condition is achieved in about 2 months. The pockets shrink little by little but steadily, to a few millimeters after about 3 months. Some patients continued in this condition, while in other cases the pockets closed almost completely as the days passed and a complete cure was achieved.

Example 7

Five periodontal disease patients with end-stage symptoms were treated by first disinfecting the affected parts with the present bactericidal disinfectant and then injecting the "novel *Lactobacillus* preparation" into the affected parts. The results are shown in Table 27.

TABLE 27

Therapeutic effects of the treatment method of the present invention on periodontal disease with end-stage symptoms ("novel Lactobacillus preparation" used as Lactobacillus preparation)

| Patient Name | Age | Sex | Site | Principal pathogens | Therapeutic progress and results |
|---|---|---|---|---|---|
| H.M. | 64 | M | ⌐3⌐ ⌐4⌐ | *P. gingivalis* *A. actino.* | Pathogens, halitosis eliminated by day 4, bleeding, swelling by day 7. Gum condition improved from day 15, tooth looseness improved somewhat. By day 60 gum tissue began to regenerate bit by bit, and pocket was somewhat shallower. Gum appearance improved, and by day 120 the teeth were no longer loose and gums had mainly recovered. By day 180 the pocket had mainly closed and the patient was cured. |
| K.N. | 67 | F | ⌐4 6⌐ ⌐2 | *P. gingivalis* *Fusobacterium* | Generally same progress as above, almost completely cured. |
| N.T. | 72 | F | ⌐2 3 4⌐ | *P. gingivalis* *P. intermedia* | Pathogens, halitosis eliminated by day 5, but bleeding, discharge continued till day 10. Gums somewhat improved by day 30, but tooth looseness and pocket depth were unchanged. Treatment was continued for 90 days and there appeared to be slight improvement, but ultimately the teeth were extracted. |
| N.M. | 59 | M | ⌐6 | *P.gingivalis* | Halitosis, pathogens eliminated by day 3. Bleeding stopped by day 5. Discharge stopped on day 7. Gum hue, elasticity tended to improve from day 15. Tooth looseness improved somewhat from day 25, gone by day 60. 27 mm gum pocket grew shallower, to 15 mm by day 90. Gum condition recovered and periodontal pocket 12 mm by day 120, 4 mm and almost cured by day 180. Alveolar bone considerably regenerated. |
| K.K. | 63 | M | ⌐5 6⌐ | *P. gingivalis* *B. forsythus* *E. corrodens* | Progress was slower than above but similar, and a cure was achieved in about 9 months. |

Example 8

Five periodontal disease patients with end-stage symptoms were treated by first disinfecting the affected parts with the present bactericidal disinfectant and then injecting the "novel *Lactobacillus* preparation containing antibiotics" into the affected parts. The results are shown in Table 28.

TABLE 28

Therapeutic effects of the treatment method of the present invention on periodontal disease with end-stage symptoms ("novel Lactobacillus preparation containing antibiotics" used as Lactobacillus preparation)

| Patient Name | Age | Sex | Site | Principal pathogens | Therapeutic progress and results |
|---|---|---|---|---|---|
| Y.M. | 77 | M | ⌊2 3⌋ | A. actino. Fusobacterium | Pathogens, halitosis eliminated by day 3 of administration, bleeding, discharge gone by day 5. Gum condition improved and tooth looseness slightly better by day 10. By day 30 alveolar bone regenerated somewhat and tooth looseness almost gone. Pocket grew shallower bit by bit, to 10 mm by day 60. by day 120 gums had recovered and pocket depth was about 5 mm, and a cure was expected with continued treatment |
| W.T. | 58 | F | ⌊3 4 5⌋ | P. gingivalis W. recta | Virtually the same progress as above |
| V.M. | 69 | M | ⌈5 5⌉ | P. gingivalis W. recta | Pathogens, halitosis eliminated by day 4. Bleeding, discharge gone by day 7. Gum hue, elasticity, swelling improved from day 12, mainly recovered by day 30. Pocket gradually smaller, to 10 mm or less by day 80. Tooth looseness improved by day 60 so that hard foods could be eaten. Mainly cured by day 150. |
| E.M. | 64 | F | ⌊3 5⌋ | A. actino W. recta | Progress mainly the same as above, although somewhat slower. |
| H.T. | 50 | F | ⌈6 5⌉ | P. gingivalis A. actino P. intermedia | Pathogens disappeared by day 5, gum hue, elasticity somewhat improved by day 20, but little difference in alveolar bone, tooth looseness improved somewhat but teeth eventually extracted. |

Comparative Example 4

As a comparative example, five periodontal disease patients with end-stage symptoms were treated as a conventional treatment with a method called "guided tissue regeneration" using Emdogain, which has been spotlighted as a revolutionary treatment. The results are shown in Table 29.

TABLE 29

Therapeutic effects of guided tissue regeneration in periodontal disease with end-stage symptoms

| | Average therapeutic progress and results for 5 patients |
|---|---|
| Guided tissue regeneration | A new technique was attempted, but there was no improvement and the teeth had to be extracted |

When periodontal disease was in the end stage, there was an unavoidable feeling of being too late with the conventional treatment method, and ultimately the teeth had to be extracted. Although extraction could be avoided and the teeth maintained by surgical methods, the disease reoccurred repeatedly, and ultimately extraction was only delayed in many cases. By contrast, using the treatment method of the present invention, the causal bacterial were rapidly eliminated and causal factors removed, and subsequent tissue regeneration effects could be expected from a combination of the two, so that in 70% to 80% of cases extraction was unnecessary and the teeth were saved even without a complete cure.

What is claimed is:

1. A method for treating periodontal disease, comprising disinfecting a part affected with periodontal disease with a bactericidal disinfectant containing 500 ppm to 1,500 ppm of trivalent ferric ions and 500 ppm to 2,000 ppm of L-ascorbic acid together with 200 ppm to 2,000 ppm of one or more members of the group consisting of sorbic acid, benzoic acid and para-hydroxybenzoic acid esters, and then infusing a preparation containing a *Lactobacillus casei* (FERM P-19443) into the part affected with periodontal disease.

2. The method for treating periodontal disease according to claim 1, wherein the preparation containing the *Lactobacillus casei* further contains antibiotics.

3. The method for treating periodontal disease according to claim 2, wherein the antibiotics are amoxicillin (AMPC), erythromycin (EM), fradiomycin (FRM) and cefaclor (CCL).

4. The method for treating periodontal disease according to either claim 2 or claim 3, wherein 2,000 mg of amoxicillin (AMPC), 500 mg of erythromycin (EM), 500 mg of fradiomycin (FRM) and 500 mg of cefaclor (CCL) are contained in 100 g of preparation containing the *Lactobacillus casei*.

* * * * *